United States Patent
Curley, Jr. et al.

(10) Patent No.: US 7,585,894 B2
(45) Date of Patent: Sep. 8, 2009

(54) 4-[(E)-2-(5,6,7,8-TETRAHYDRO-5,5,8,8-TETRAMETHYL-2-NAPTHALENYL)-1-PROPENYL]BENZOIC ACID ANALOGS AND METHOD OF MANUFACTURE AND USE THEREOF

(75) Inventors: Robert W. Curley, Jr., Dublin, OH (US); Margaret Clagett-Dame, Deerfield, WI (US); Michael D. Collins, Agoura Hills, CA (US); Victoria V. Abzianidze, Columbus, OH (US)

(73) Assignee: Wisconsin Alumni Research Foundation, Madison, WI (US)

( * ) Notice: Subject to any disclaimer, the term of this patent is extended or adjusted under 35 U.S.C. 154(b) by 235 days.

(21) Appl. No.: 11/428,165

(22) Filed: Jun. 30, 2006

(65) Prior Publication Data

US 2007/0015717 A1 Jan. 18, 2007

Related U.S. Application Data

(60) Provisional application No. 60/695,564, filed on Jun. 30, 2005.

(51) Int. Cl.
*A61K 31/351* (2006.01)
*C07D 309/10* (2006.01)
(52) U.S. Cl. ...................... 514/460; 549/418
(58) Field of Classification Search ................. 514/460; 549/418
See application file for complete search history.

(56) References Cited

U.S. PATENT DOCUMENTS

| 4,326,055 A | 4/1982 | Loeliger |
| 5,516,792 A | 5/1996 | Curley, Jr. et al. |
| 5,574,177 A | 11/1996 | Curley, Jr. et al. |
| 5,599,953 A | 2/1997 | Curley, Jr. et al. |
| 5,663,377 A | 9/1997 | Curley, Jr. et al. |
| 6,117,845 A | 9/2000 | Clagett-Dame et al. |

OTHER PUBLICATIONS

Lotan et al. J. Nutr. Growth Cancer (1983) vol. 1, No. 2, pp. 71-76.*
A. Krust, PH. Kastner, M. Petkovich, A. Zelent and P. Chambon; A Third Human Retinoic Acid Receptor, hRAR-y; Proc. Natl. Acad. Sci. USA, vol. 86, pp. 5310-5314, Jul. 1989.
Daniele Simoni, Riccardo Randanin, Riccardo Baruchello, Marinella Roberti, Marcello Rossi, Stefani Grimaudo, Natale D'Alessandro, Francesco Paolo Invidiata, and Manlio Tolomeo.
Retinoic Acid and Analogs as Potent Inducers of Differentiation and Apoptosis. New Promising Chemopreventive and Chemotherapeutic.
Agents in Oncology; Pure Appl. Chem., vol. 73, No. 9, pp. 1437-1444, 2001.

* cited by examiner

*Primary Examiner*—Taofiq A Solola
(74) *Attorney, Agent, or Firm*—Joseph T. Leone, Esq.; DeWitt Ross & Stevens S.C.

(57) ABSTRACT

Analogs of 4-[(E)-2-(5,6,7,8-tetrahydro-5,5,8,8-tetramethyl-2-napthalenyl)-1-propenyl]benzoic acid and methods of manufacture and use thereof, such as for use in cancer prevention and treatment.

15 Claims, 17 Drawing Sheets

Aldose Sugar Analogs of 4-HBTTNPB (Oxygen-linked)

(Methylene-linked)

*In the above Figure, 4-HTTNPB = 4-HPTTNPB

*In the above Figure, 4HTTNPB = 4-HPTTNPB

4-[(E)-2-(5,6,7,8-TETRAHYDRO-5,5,8,8-TETRAMETHYL-2-NAPTHALENYL)-1-PROPENYL]BENZOIC ACID ANALOGS AND METHOD OF MANUFACTURE AND USE THEREOF

PRIORITY APPLICATIONS

Pursuant to 35 U.S.C. § 120, benefit is hereby claimed to U.S. Patent Application Ser. No. 60/695,564 filed on Jun. 30, 2005 as regards the entire disclosure therein.

RELATED PATENTS AND RELATED COPENDING APPLICATIONS

The present invention is related to U.S. Pat. Nos. 6,117,845; 5,663,377; 5,599,953; 5,574,177; and 5,516,792, which are incorporated herein by reference. The present invention is also related to co-pending U.S. patent application Ser. No. 11/416,907, filed on May 3, 2006, which is also incorporated herein by reference.

STATEMENT REGARDING FEDERALLY SPONSORED RESEARCH OR DEVELOPMENT

This invention was made with United States government support awarded by the following agencies:
NIH CA49837
The United States has certain fights in this invention.

FIELD OF THE INVENTION

The inventive field includes analogs of 4-[(E)-2-(5,6,7,8-tetrahydro-5,5,8,8-tetramethyl-2-napthalenyl)-1-propenyl]benzoic acid and methods of manufacture and use thereof, such as for use in cancer prevention and treatment.

BACKGROUND OF THE INVENTION

Breast cancer is the cause of thousands of deaths among females every year. (See A Snapshot of Breast Cancer, National Cancer Institute (August 2005)). Surgical intervention has saved the lives of many women. However, radical and partial mastectomies can be physically and emotionally debilitating. Surgery in combination with chemotherapy may still expose patients to the possibility of recurrence.

Massive research efforts have been directed to researching and developing drugs and other therapies (such as radiation, immunotherapy and vaccine) to treat and/or prevent breast cancer. Retinoic acid is a known metabolite of vitamin A. Retinoic acid and certain analogs thereof appear to be necessary for maintenance of normal epithelial tissue differentiation. Such analogs of retinoic acid may also be able to reverse the metaplastic condition of hamster trachea in vitamin A deficient epithelial tissue. (See Newton et al., *Cancer Res* 40:3413-3425 (1980)). Retinoic acid and certain amide analogs thereof have also been investigated for use as chemotherapeutic agents. (See Moon et al., *Cancer Res* 39:1339-1346 (1979)). Other retinoic acid analogs such as retinyl acetate, 13-cis-retinoic acid and glucuronide analogs have also been shown to display some cancer preventive activity including breast cancer preventive activity. (See Hill D L et al., *Ann Rev Nutrition*, 12:161-181 (1992))(See also Mehta R G et al., *Oncology*, 48:1505-1509 (1991)). Stilbene derivatives of retinoic acid have been suggested as possible agents for use in oncology. (See Simoni D et al., Retinoic Acid and Analogs as Potent Inducers of Differentiation and Apoptosis: New Promising Chemopreventative and Chemotherapeutic Agents in Oncology, *Pure Appl Chem*, 73:1437-1444 (2001)). Aromatic analogs of retinoic acid, such as 4-[(E)-2-(5,6,7,8-tetrahydro-5,5,8,8-tetramethyl-2-napthalenyl)-1-propenyl]benzoic acid ("TTNPB"), were also disclosed in Simoni et al.

The structure of retinoic acid ("RA") is shown below.

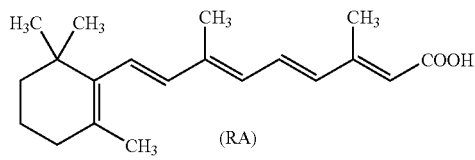

Retinoid compounds are involved in the modulation of a wide variety of cellular processes such as proliferation, differentiation and apoptosis. Retinoid compounds have been investigated for use as cancer chemotherapeutic agents, but undesirable side effects have been problematic. Arotinoid compounds are a class of aromatic retinoid compounds. Arotinoid compounds have high biological activity but also impart undesirable toxicity. For example, the structure of TTNPB is also shown below.

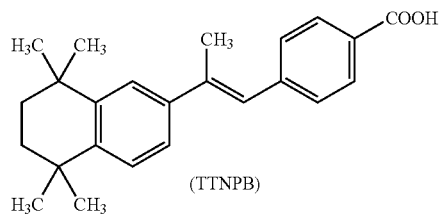

Toxicity has, however, been a significant obstacle to developing retinoic acid and the analogs thereof. (See Biesalski H K, *Toxicology*, 57:117-161 (1989)). The observed side effects include: teratogenicity, hepatotoxicity, blood lipid abnormalities, scaly skin, hair loss and headaches. Other research has sought to discover new retinoic acid analogs having increased potency and/or reduced toxicity for use as cancer preventative agents. For example, it has been reported that N-(4-hydroxyphenyl) retinamide ("4-HPR") displays chemopreventive activity toward breast cancer. (See Moon et al., *Cancer Res*, 39:1339-1346 (1979)). It has also been reported that the combination of 4-HPR and calcium glucarate has increased and synergistic breast cancer chemopreventive activity in carcinogen-induced rat mammary tumors. (See, Abou-Issa H M et al., *Proc Natl Acad Sci USA*, 85:4181-4184 (1988). However, the 4-HPR still displayed teratogenic potential in rat, mice and rabbit studies. (See Kenel M F et al., Teratogenicity of N-(4-hydroxyphenyl)-all-trans Retinamide in Rats and Rabbits, *Teratogenesis, Carcinogenesis and Mutagenesis*, 8:1-11 (1988))(See also Kochhar D M et al., Retinamides: Hydrolytic Conversion of Retinoylglycine to Retinoic Acid in Pregnant Mice Contributes to Teratogenicity, *Teratology*, 45:175-185 (1992)). It has also been reported that 4-HPR impairs night vision in human patients. (See Kaiser-Kupter M I et al., Abnormal Retinal Function Associated with Fenretinide, A Synthetic Retinoid Renretinide (HPR), *Eur J Cancer Clin Oncol*, 25:805-808 (1989)).

The structure of 4-HPR is shown below.

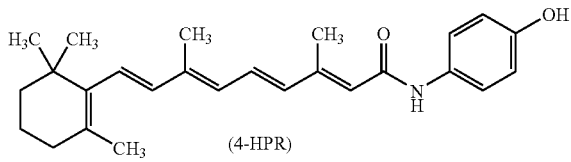
(4-HPR)

The ketone analog of 4-HPR is 4-HBR. The structure of 4-HBR is shown below. The properties (and synthesis thereof) of 4-HBR is disclosed in U.S. Pat. No. 6,117,845 to Clagett-Dame et al., which also discloses synthesis of various sugar-analogs of 4-HBR.

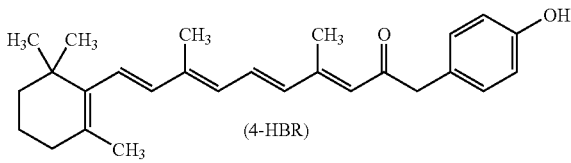
(4-HBR)

4-HBR and analogs thereof possess anti-neoplastic activity and are useful in preventing (i.e., prophylactic treatment) and/or treating neoplastic growth in mammals.

Despite recent advances in synthesis of stable and active analogs of retinoid acid, there remains a need for more potent and less toxic analogs and derivatives of retinoic acid and TTNPB, particularly such drugs useful for prophylactic treatment and treatment of many cancers including breast cancer.

SUMMARY OF THE INVENTION

One aspect of the invention is a compound according to the formula

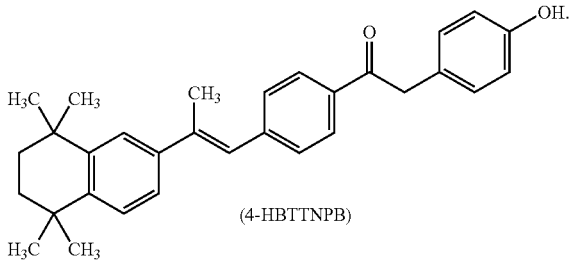
(4-HBTTNPB)

The compound may also be pharmaceutically suitable salts or solvates thereof, whereby the 4-HBTTNPB compound or pharmaceutically suitable salts or solvates thereof may be administered to a human for the prophylactic treatment of breast cancer or to treat breast cancer.

Another aspect of the invention is a compound according to the formula

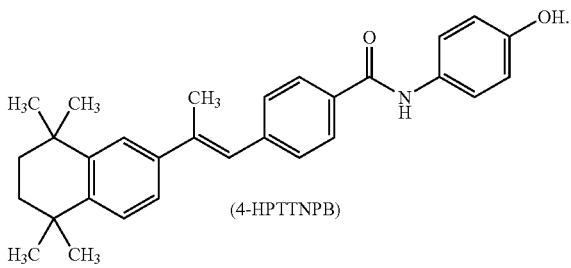
(4-HPTTNPB)

The compound may also be pharmaceutically suitable salts or solvates thereof, whereby the 4-HPTTNPB compound or pharmaceutically suitable salts or solvates thereof may be administered to a human for the prophylactic treatment of breast cancer or for treating breast cancer.

Another aspect of the invention is a compound according to the formula

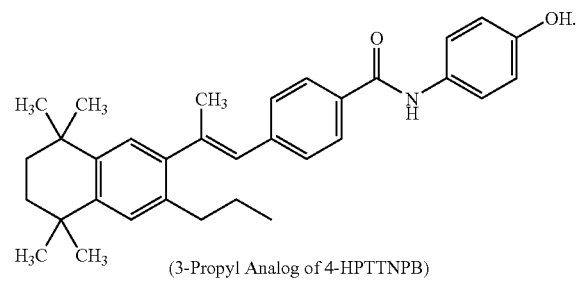
(3-Propyl Analog of 4-HPTTNPB)

The compound may also be pharmaceutically suitable salts or solvates thereof, whereby the 3-propyl analog of 4-HPTT-NPB compound or pharmaceutically suitable salts or solvates thereof may be administered to a human for the prophylactic treatment of breast cancer or to treat breast cancer.

A compound according to the formula (I)

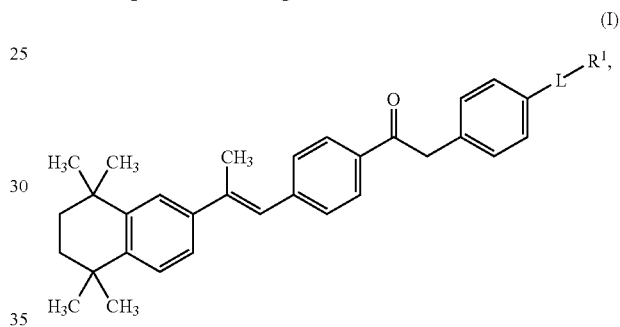

wherein L is a member selected from the group consisting of a single bond, $CH_2$, and O, and, wherein $R^1$ is a member selected from the group consisting of an aldose moiety,

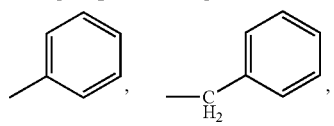

and, $C_{1-6}$ straight or branched chain alkyl group, and salts, esters and solvates thereof.

Preferably, the aldose residue moiety is:

(IIa)

(IIb)
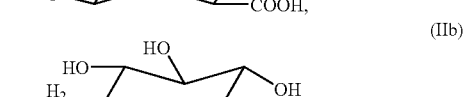

(IIc)
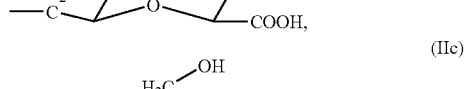

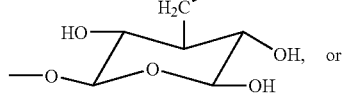 or

-continued

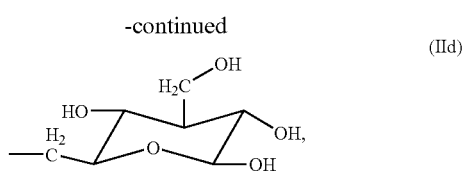
(IId)

The compound may also be pharmaceutically suitable salts, esters or solvates thereof, whereby such compounds or such salts, esters or solvates thereof may be administered to a human for the prophylactic treatment of breast cancer or for treating breast cancer. Where L is O, the $C_{1-6}$ straight or branched chain alkyl group may be:

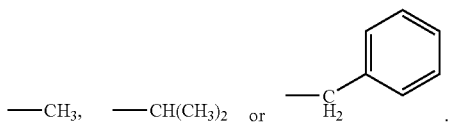

DETAILED DESCRIPTION OF THE PREFERRED EMBODIMENTS

Figure 1A:
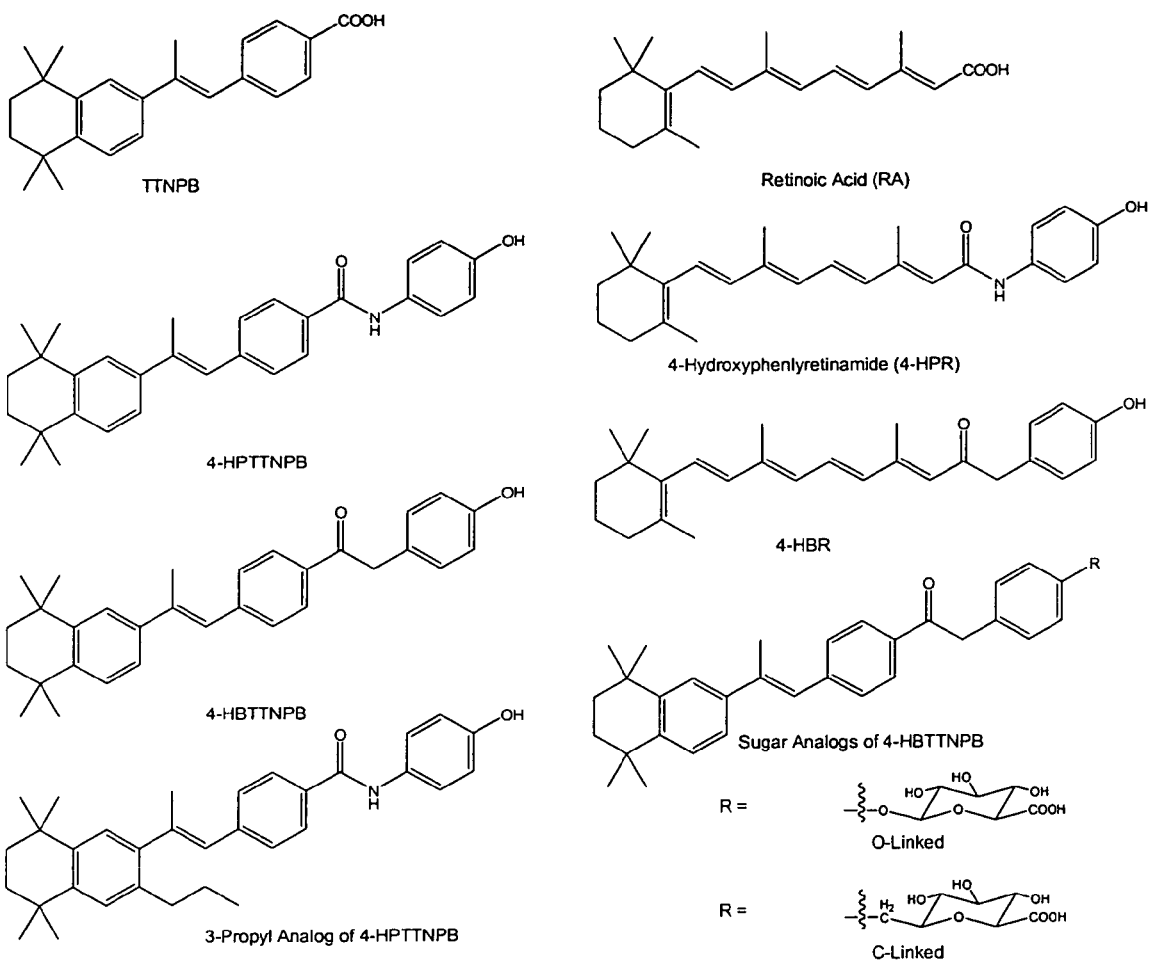
FIG. 1A shows the structure of various compounds referred to in the specification.
Figure 1B:
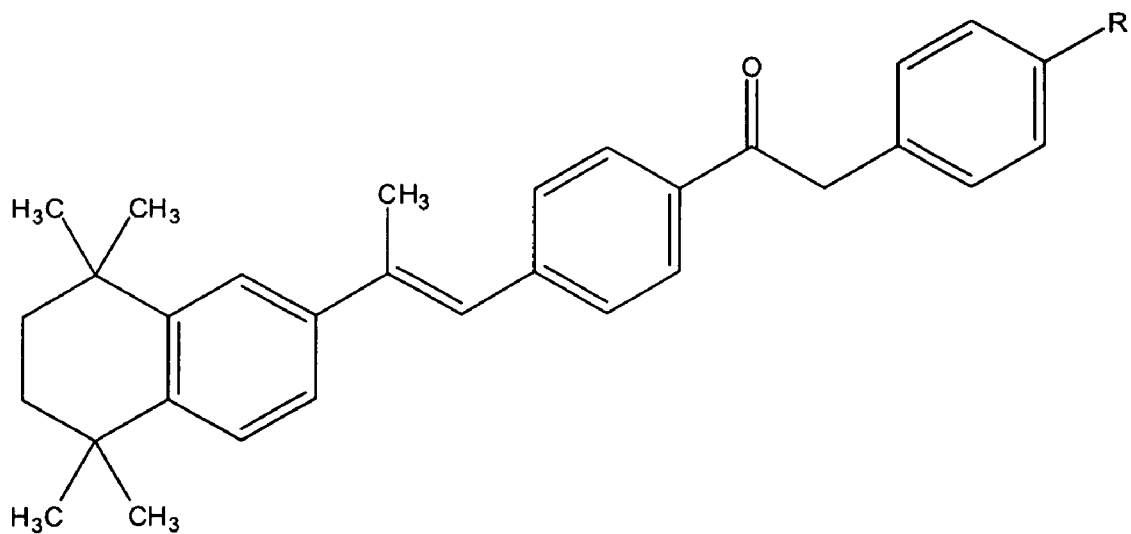
FIG. 1B shows the structure of oxygen and methylene linked sugars of 4-HBTTNPB.
Figure 1B:
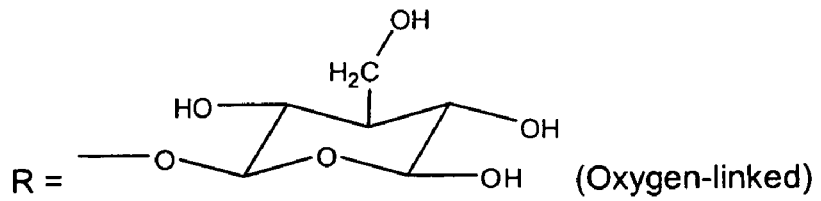
Figure 1B:
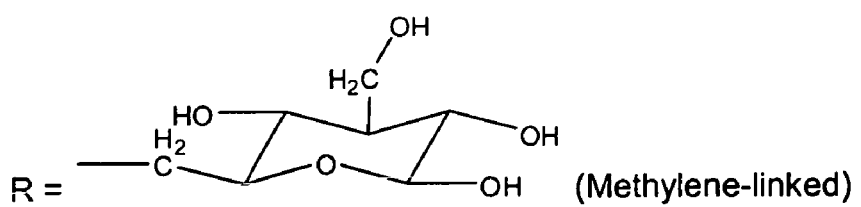

The structure of 4-[(E)-2-(5,6,7,8-tetramethyl-2-napthalenyl)-1-propenyl]benzoic acid (TTNPB) is set forth in FIG. 1A. TTNPB and other analogs of retinoic acid show resistance to metabolism and possess significant chemotherapeutic activity modulating cell growth and apoptosis. TTNPB is a potent but toxic aromatic analog of retinoic acid. TTNPB selectively binds to the retinoic acid receptor ("RAR"). However, TTNPB does not bind to the retinoid X receptor ("RXR"). As such, TTNPB is advantageous over retinoic acid in that it selectively binds to the RAR. Retinoic acid does, however, isomerize and bind to the RXR.

The carboxylic acid group in the retinoic acid molecule is covalently linked (via an amide linkage) to a para-hydroxyphenyl amine thus yielding the 4-hydroxyphenylretinamide ("4-HPR"). 4-HPR has chemopreventative-chemotherapeutic activity against breast cancer. 4-HPR is also significantly less toxic than retinoic acid. In culture, 4-HPR inhibits growth of cancer cells by apoptosis. In contrast, retinoic acid and TTNPB cause growth arrest by causing differentiation. 4-HPR may also show RAR-independent activity. (See U.S. Pat. No. 6,117,845).

Figure 2:
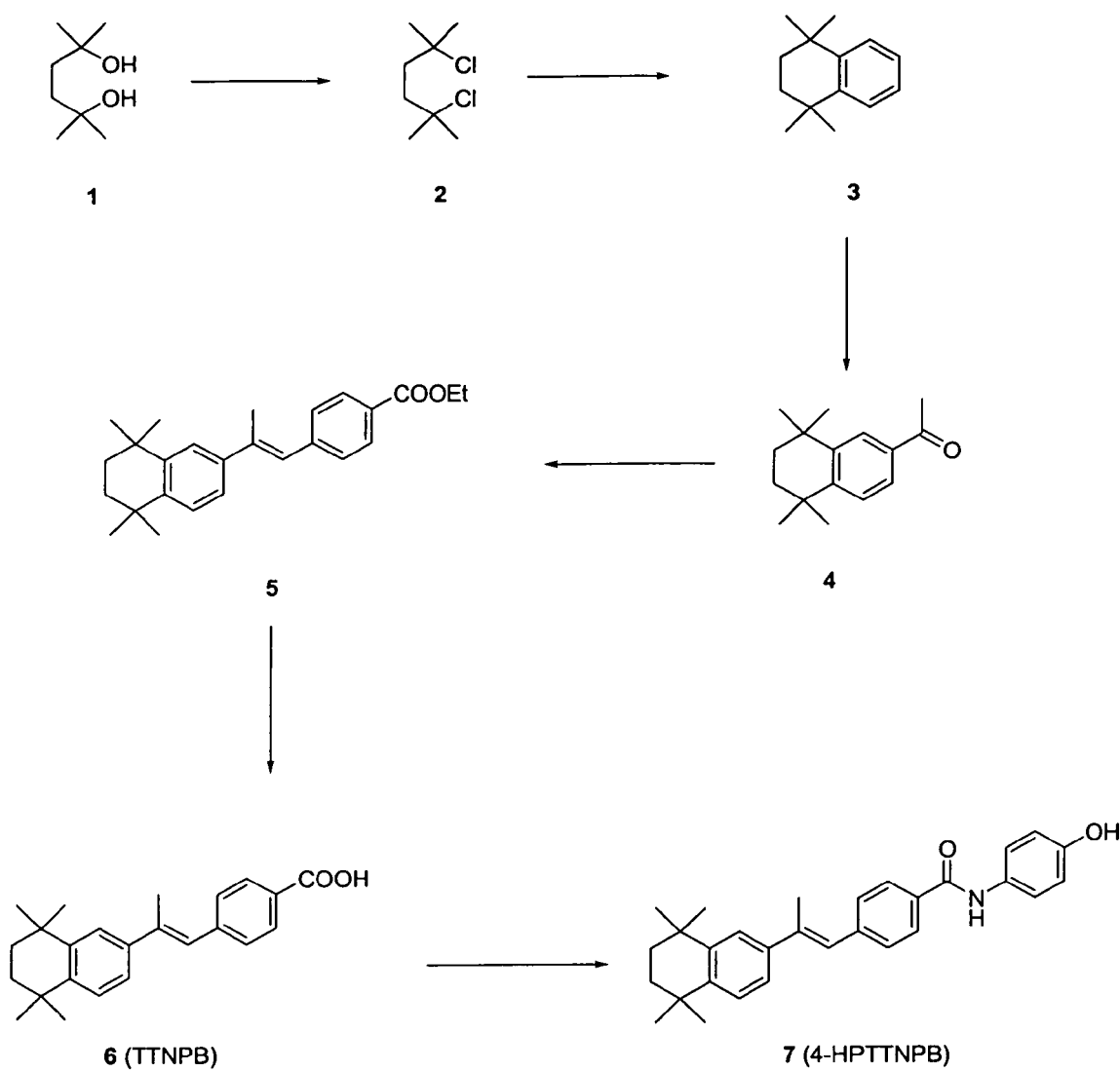
FIG. 2 shows a reaction scheme for the synthesis of TTNPB and 4-HPTTNPB.
Figure 3:
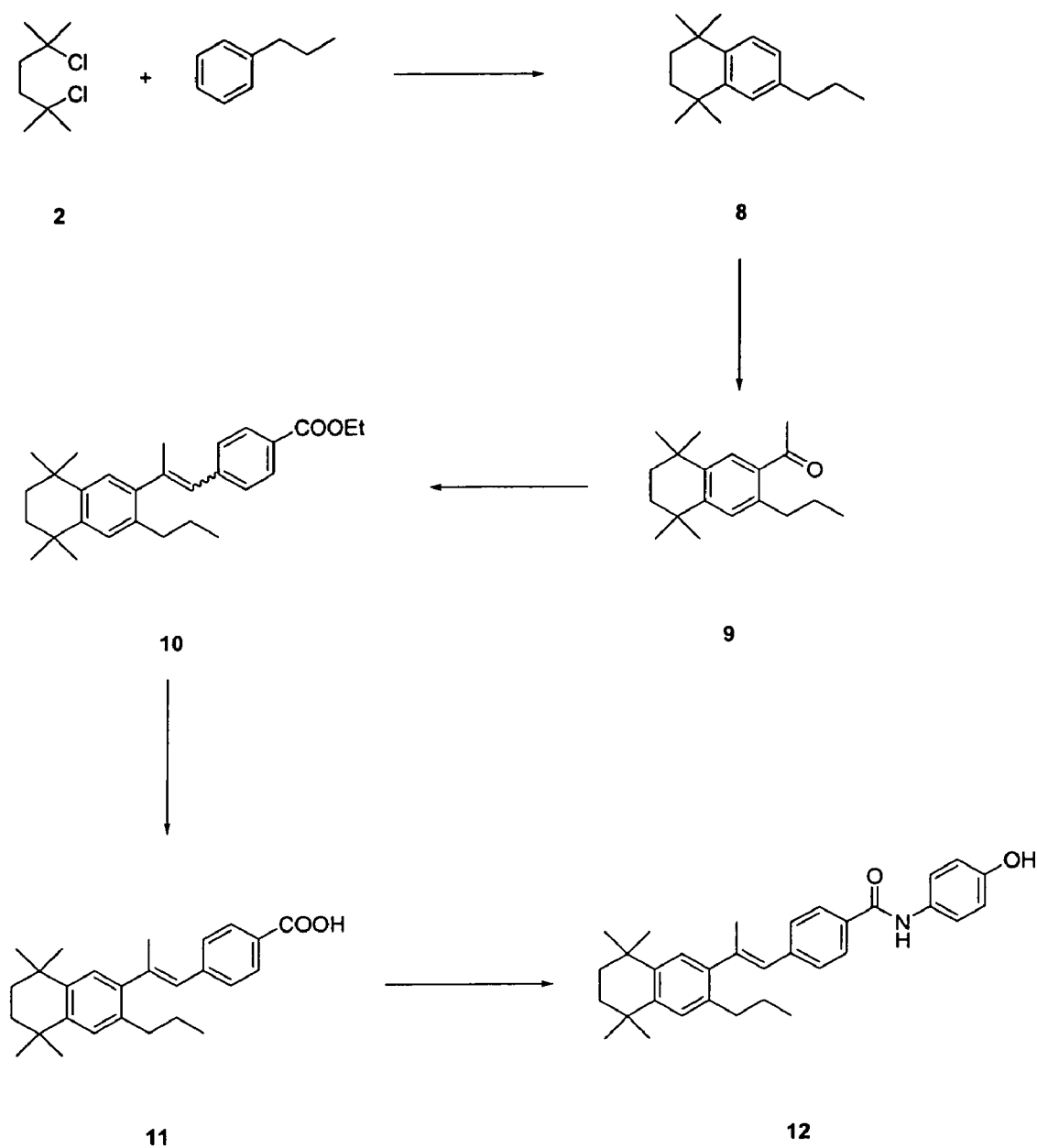
FIG. 3 shows a reaction scheme for the synthesis of propyl analogs of TTNPB and 4-HPTTNPB.
Figure 4:
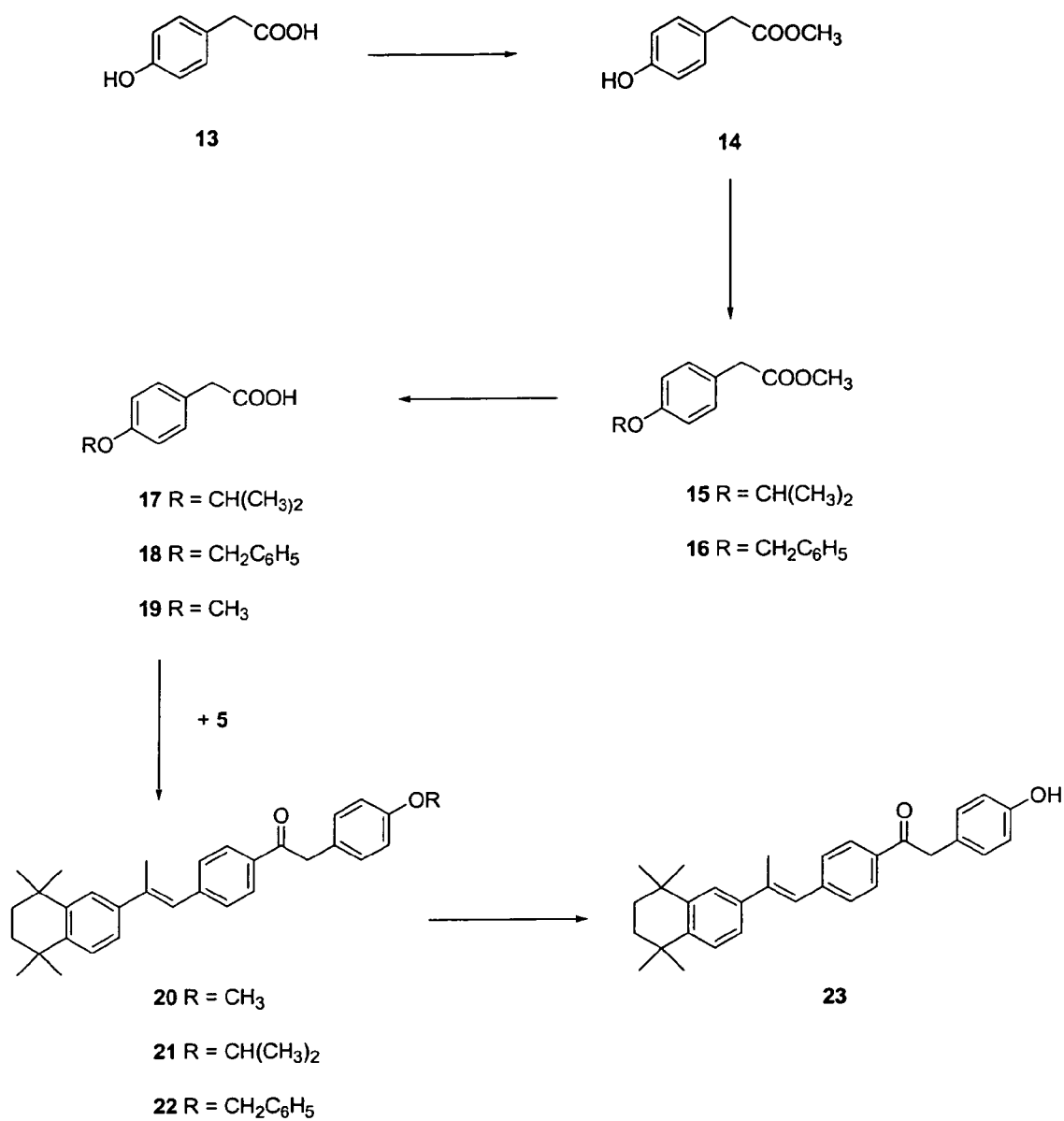
FIG. 4 shows a reaction scheme for the synthesis of 4-HBTTNPB.
Figure 5:
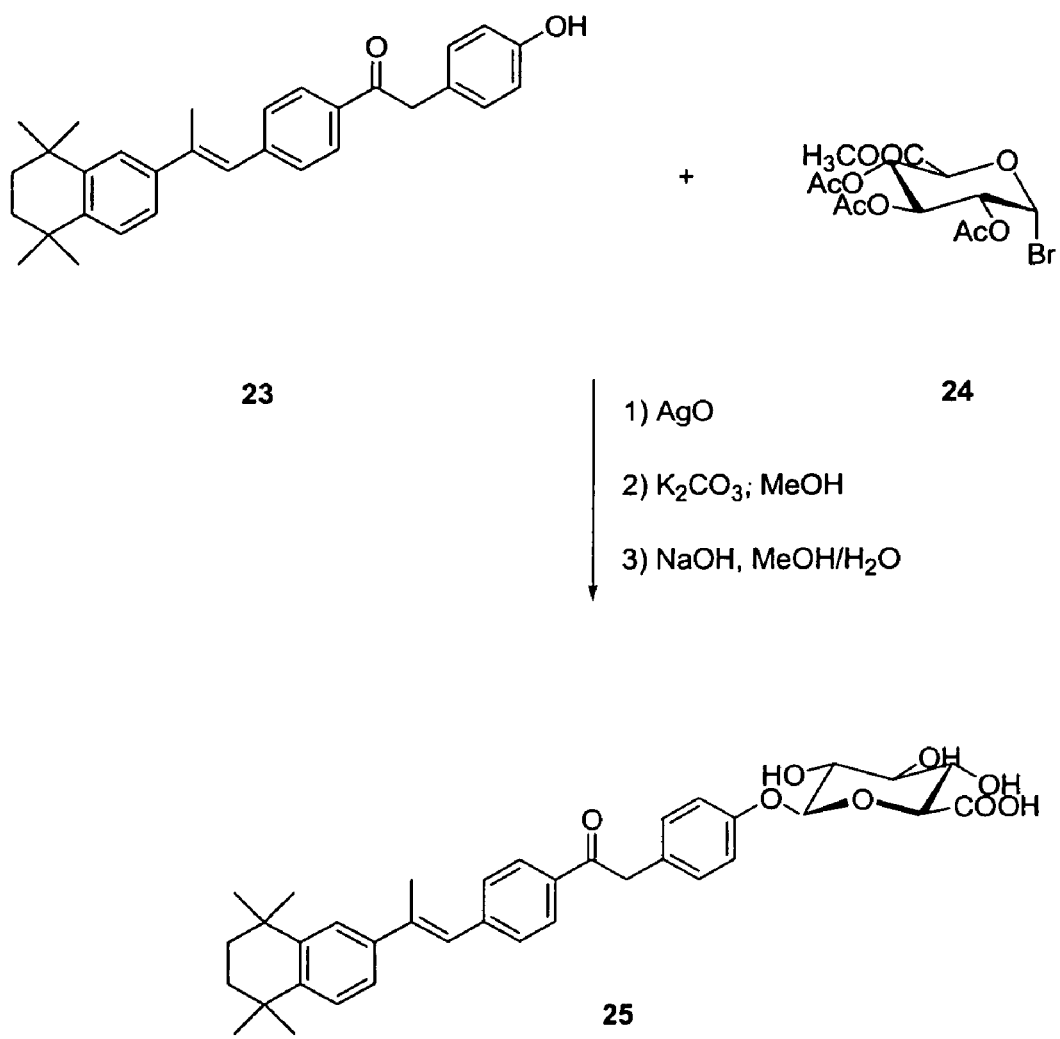
FIG. 5 shows a reaction scheme for the synthesis of an oxygen-linked sugar analog of 4-HBTTNPB.
Figure 6:
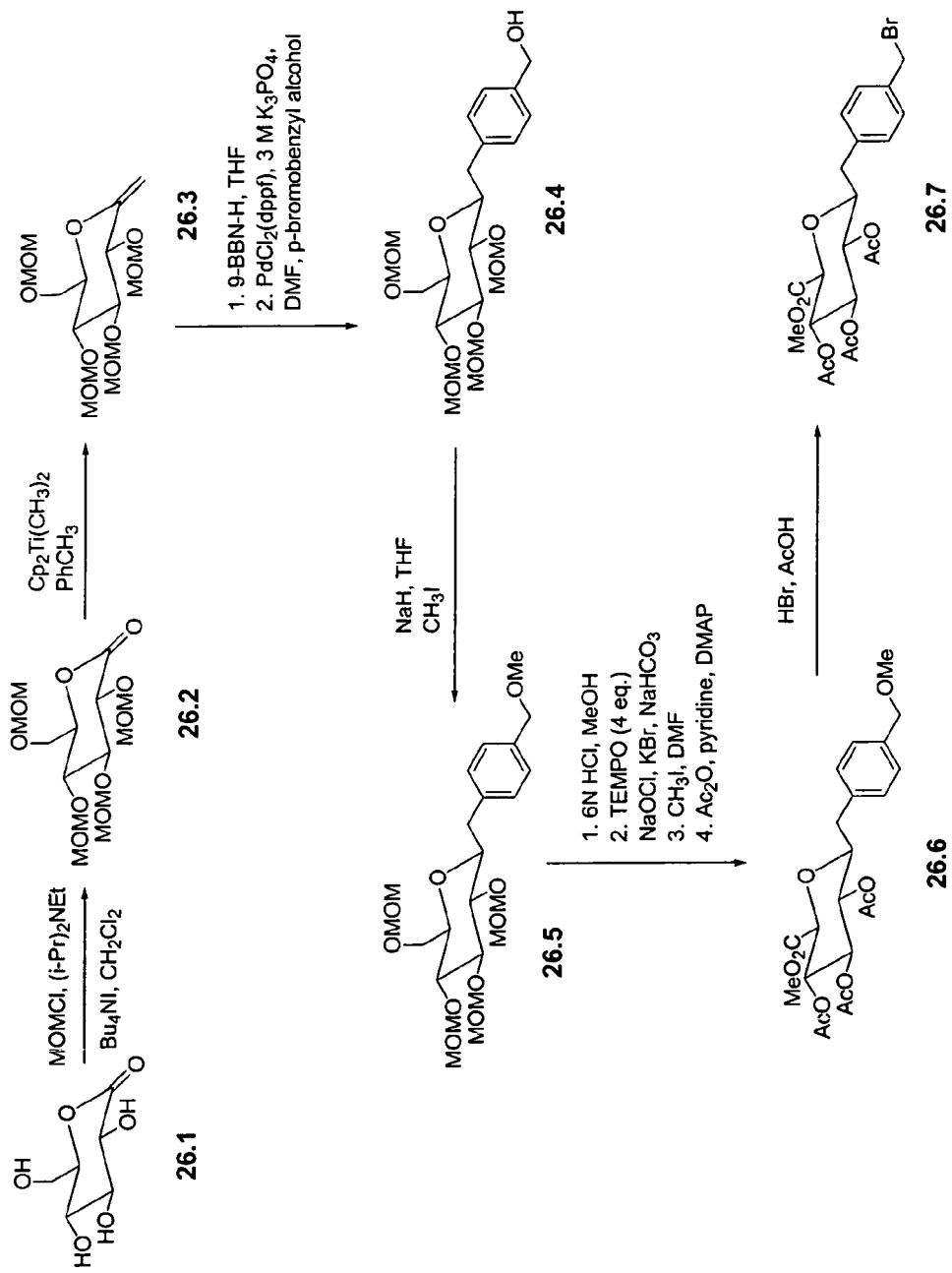
FIG. 6 shows a reaction scheme for the synthesis of $CH_2$-linked (methylene-linked) sugar analogs of 4-HBTTNPB.
Figure 7:
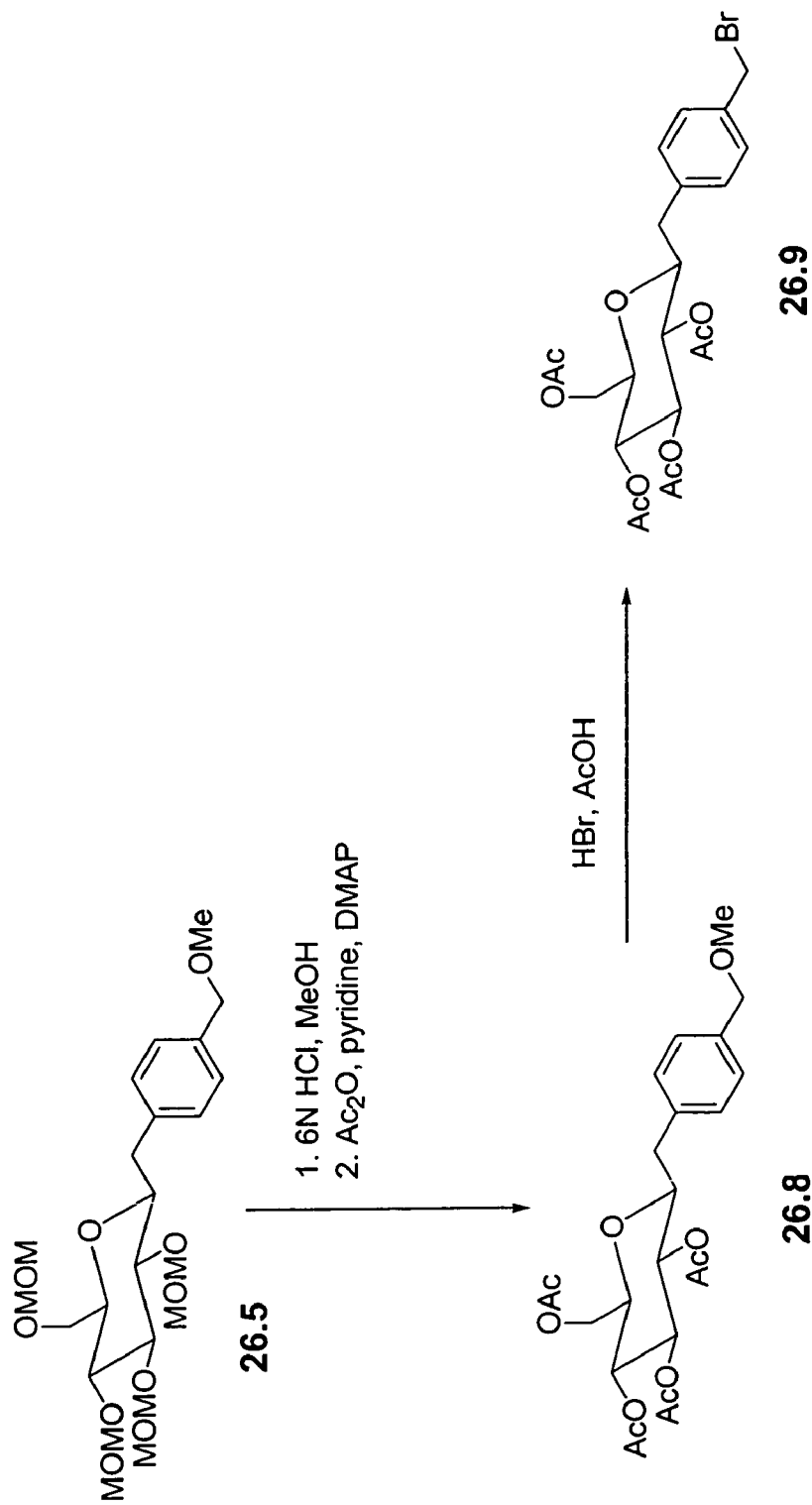
FIG. 7 shows a reaction scheme for another synthesis of $CH_2$-linked sugar analogs of 4-HBTTNPB.

As shown in FIG. 2, the carboxylic acid group of TTNPB is covalently linked (via an amide linkage) to a para-hydroxyphenyl amine thus yielding the 4-HPTTNPB. As shown in FIG. 3, 3-propyl analogs of TTNPB and 4-HPTTNPB were synthesized (see, compounds 11 and 12 herein below). Without being bound to any theory, it appears that the 3-propyl analog of 4-HPTTNPB (compound 12) will not bind to the RAR even it is hydrolyzed in vivo to compound 11. It is further theorized that the 3-propyl analog of 4-HPTTNPB will not bind to the RAR protein for the same reason. As such, it is theorized that the 3-propyl analog of 4-HPTTNPB is sufficiently non-toxic for pharmaceutical use in humans (i.e., pharmaceutically suitable) because it will not bind to the RAR or RXR proteins.

Alternatively, it is theorized that the ketone group in compounds 20, 21, 22, 23 (4-HBTTNPB), 25 (oxygen-linked glucuronide of 4-HBTTNPB), 29 (methylene-linked glucuronide of 4-HBTTNPB), 30 (methylene-linked glucose of 4-HBTTNPB), and 33 (oxygen-linked glucose of 4-HBTTNPB) functions similar to the amide group in 4-HPTTNPB. It is understood that the glucose moiety may be any of the various moieties derived from an aldose such as a monosaccharide, a monocarboxylic acid, a dicarboxylic acid, a polyhydroxy alcohol or an aldehydo acid. (See Morrison and Boyd, *Organic Chemistry*, 3rd:1075 (1973)). For example, within the family of aldose derivatives, glucuronic acid is an aldehydo acid that forms a glucuronide derivative moiety. The ketone group will also not bind to the RAR or RXR proteins. Compound 20 is E-4-[2-methyl-2-(1,1,4,4-tetramethyl-1,2,3, 4-tetrahydronapth-7-yl)-vinyl]phenyl-2'-(4'-methoxyphenyl)-1'-ethanone. Compound 21 is E-4-[2-methyl-2-(1,1,4,4-tetramethyl-1,2,3,4-tetrahydronapth-7-yl)-vinyl]-phenyl-2'-(4'-isopropoxyphenyl)-1'-ethanone. Compound 22 is E-4-[2-methyl-2-(1,1,4,4-tetramethyl-1,2,3,4-tetrahydronapth-7-yl)-vinyl]-phenyl-2'-(4'-benzyloxyphenyl)-1'-ethanone. These ketone-containing compounds were synthesized as set forth herein below and exhibit potent activity inhibiting tumor cell proliferation such that they are suitable for the prophylactic treatment of breast cancer and for treating breast cancer. Unexpectedly, sugar-containing analog compounds 25, 29, 30 and 33 also have enhanced desirable properties such as solubility, bioavailability and low toxicity.

EXAMPLES

Synthesis and characteristics of various retinoic acid derivatives is described in U.S. Pat. Nos. 6,117,845; 4,578, 498; and 4,326,055, whereby the entire disclosure of each hereby incorporated herein by reference. In addition, instant FIGS. 2-8 set forth additional synthetic methods for making the various novel compounds disclosed herein.

2,5-Dimethylhexane-2,5-diol and propyl benzene are commercially available from Aldrich Chemical Company, Milwaukee, Wis. Other reagents may be commercially available from, among others, Sigma-Aldrich, St. Louis, Mo. and Aldrich Chemical Company. Such reagents were prepared using known procedures or as set forth herein.

2,5-Dichloro-2,5-dimethylhexane (compound 2) was synthesized using a known procedure set forth in Bruson H et al., *J Am Chem Soc*, 62:36 (1940), whereby 50 g of 2,5-dimethylhexane-2,5-diol (compound 1) and 1 L of concentrated hydrochloric acid was used. Yield was measured quantitatively. Properties of compound 2 matched that reported in Bruson et al.

1,1,4,4-Tetramethyl-1,2,3,4-tetrahydronapthalene (compound 3) was synthesized using a known procedure set forth in Bruson et al. A Friedel-Crafts reaction was used, whereby 36 g of 2,5-dichloro-2,5-dimethylhexane (compound 2), 78 g of benzene, and 16 g of aluminum chloride was combined resulting in a 60% yield. Properties of compound 3 matched that reported in Bruson et al. 7-Acetyl-1,1,4,4-tetramethyltetralin (compound 4) was synthesized using a known procedure set forth in Wood T F et al., *Org Chem*, 28(9):2248 (1963), whereby 16 g of 1,1,4,4-tetramethyl-1,2,3,4-tetrahydronapthalene, 7.4 g acetyl chloride and 13.6 g of aluminum chloride was used resulting in a 92% yield. $^1$H NMR was used to confirm formation of compound 3.

Ethyl E-4-[2-methyl-2-(1,1,4,4-tetramethyl-1,2,3,4-tetrahydronapth-7-yl)-vinyl]-benzoate (compound 5) was synthesized using a known procedure set forth in Dawson M et al., *J Org Chem*, 49:5265 (1984), whereby 30 mL of 1.0 M NaCH$_2$SOCH$_3$ (or, 27 mmol) was added to 10 g diethyl p-carboxyethylbenzylphosphonate with stirring. After 0.5 hours, the red-brown solution of phosphonate anion was added to 3.45 g of 7-acetyl-1,1,4,4-tetramethyltetralin (compound 4) in 45 mL of Me$_2$SO. The reaction mixture was stirred for 4 hours. Then, 9 mL of 2.0 M NaOEt (or, 18 mmol) in EtOH was added, and the red-brown reaction mixture was stirred overnight. The reaction mixture was worked up by pouring into 10% aqueous NaHCO$_3$ (900 mL); extracting with Et$_2$O; washing with brine; and, drying over MgSO$_4$.

After filtration and removal of Et$_2$O, the residue was suspended in 6 mL hexane and allowed to stand for 4-6 hours producing gummy crystals. Recrystallization from 20% hexane/CH$_3$OH yielded 4.68 g (83% yield) of ethyl E-4-[2-methyl-2-(1,1,4,4-tetramethyl-1,2,3,4-tetrahydronapth-7-yl)-vinyl]-benzoate (compound 5) which was a colorless solid. Properties of compound 5 matched that reported in Dawson et al. HPLC (octadecylsilane 4.6×250 mm column, CH$_3$OH/H$_2$O 85:15, UV 310 nm, flow rate 1.0 mL/min, t$_r$=44.5 min.).

E-4-[2-methyl-2-(1,1,4,4-tetramethyl-1,2,3,4-tetrahydronapth-7-yl)-vinyl]-benzoic acid (TTNPB; compound 6) was synthesized by hydrolyzing ethyl E-4-[2-methyl-2-(1,1, 4,4-tetramethyl-1,2,3,4-tetrahydronapth-7-yl)-vinyl]benzoate (compound 5) in 6M aqueous KOH. Yield was 90%. M$_p$ was 247-248° C. (from acetic acid). HPLC (octadecylsilane 4.6×250 mm column, CH$_3$OH/H$_2$O 85:15, UV 310 nm, flow rate 1.0 mL/min, t$_r$=8.5 min.): $^1$H-NMR (300 MHz, (CD$_3$)$_2$SO), δ 1.21 (s, 6H), 1.25 (s, 6H), 1.62 (s, 4H), 2.21 (s, 3H), 6.83 (s, 1H), 7.28 (s, 2H), 7.44 (s, 1H), 7.70 (AB, 4H, J$_{AB}$=8.06 Hz), acid OH exchanges with H$_2$O from the solvent.

E4-[2-methyl-2-(1,1,4,4-tetramethyl-1,2,3,4-tetrahydronapth-7-yl)-vinyl]-benzoic acid 4-hydroxyanilide (4-HPTTNPB; compound 7). To a suspension of 3.1 g (8.91 mmol) of compound 6 and 0.86 mL (10.7 mmol) of pyridine in 30 mL of anhydrous tetrahydrofuran, 0.78 mL (10.7 mmol) of thionyl chloride was added. The mixture was stirred for 2 hours at room temperature (RT). The precipitate formed was filtered off, and the mother liquor was added to the suspension of 2.91 g (26.7 mmol) of 4-aminophenol in 20 mL of tetrahydrofuran. Stirring continued for another 20 hours at RT. The reaction mixture was then stirred into 70 mL water. The mixture was acidified with 2N hydrochloric acid. The resulting precipitate was filtered off and recrystallized from acetic acid yielding 3.64 g E-4-[2-methyl-2-(1,1,4,4-tetramethyl-1, 2,3,4-tetrahydronapth-7-yl)-vinyl]-benzoic acid 4-hydroxyanilide (compound 7) which was in the form of colorless needles. M$_p$=252-253° C. HPLC (octadecylsilane 4.6×250 mm column, CH$_3$OH/H$_2$O 85:15, UV 310 nm, flow rate 1.0 mL/min. t$_r$=14 min.); UV$_{max}$(DMSO), 297 (88 500); $^1$H-NMR (300 MHz, (CD$_3$)$_2$CO), δ 1.27 (s, 3H), 1.31 (s, 3H), 1.70 (s, 4H), 2.29 (s, 3H), 6.89 (s, 1H), 7.22 (AB, 8.96 Hz), 7.33 (s, 2H), 7.62 (s, 1H), 7.76 (AB, 4H, J$_{AB}$=8.32 Hz), 8.13 (s, OH), 9. (s, NH); $^{13}$C-NMR (75 MHz, (CD$_3$)$_2$CO), δ 17 (C$_{30}$), 34.2 (C$_{26}$, C$_{27}$, C$_{28}$, C$_{29}$), 34.9 (C$_2$, C$_3$), 36.5 (C$_1$, C$_4$), 127 (C$_{12}$), 145.1 (C$_{11}$), 198 (C$_{19}$), 116.5, 123.1, 124, 124.9, 122.1, 122.5, 123.2, 129.9, 132.5, 133.8, 142.8 (C$_{ar}$).

1,2,3,4-Tetrahydro-1,1,4,4-tetramethyl-6-propylnaphalene (compound 8) was synthesized using a known procedure (see Boehm M et al., *J Med Chem*, 37:2930 (1994)) using 20 g of 2,5-dichloro-2,5-dimethylhexane (compound 2), 26.37 g of propyl benzene, and 0.2 g of aluminum chloride producing a 9% yield. Properties matched that described in Boehm et al.

7-Acetyl-6-propyl-1,1,4,4-tetramethyltetralin (compound 9) was synthesized using a known procedure (see Wood T F et al., *J Org Chem*, 28(9):2248 (1963)) producing a 20% yield. $^1$H NMR was used to confirm the identity of the product.

Ethyl E,Z-4-[2-methyl-2-(6-propyl-1,1,4,4-tetramethyl-1, 2,3,4-tetrahydronapth-7-yl)-vinyl]-benzoates (compound 10) were synthesized according to the procedure set forth herein respecting compound 5. The resultant mixture was worked up and chromatographed using silica gel and 10% EtOAc/90% hexane to produce a mixture containing compound 10 as a colorless oil at a 16% yield. $^1$H-NMR was used to characterize the product.

E-4-[2-methyl-2-(6-propyl-1,1,4,4-tetramethyl-1,2,3,4-tetrahydronapth-7-yl)-vinyl]-benzoic acid (compound 11) was synthesized by hydrolysis of ethyl compound 10 in 6M aqueous KOH producing an 80% yield. $^1$H NMR was used to confirm the identity of the product (see Frickel F et al., U.S. Pat. No. 4,578,498) whereby the HPLC included the following materials and settings: octadecylsilane 4.6×250 mm column, CH$_3$OH/H$_2$O 85:15, UV 310 nm, flow rate 1.0 mL/min, and t$_r$=24 min.

E-4-[2-methyl-2-(6-propyl-1,1,4,4-tetramethyl-1,2,3,4-tetrahydronapth-7-yl)-vinyl]-benzoic acid 4-hydroxyanilide (compound 12) was synthesized by according to the procedure herein. The resultant mixture was worked up, extracted with ether, washed with brine, and dried over MgSO$_4$. After removal of Et$_2$O, the residue was chromatographed using silica gel and a mixture of 50% EtOAc and 50% hexane affording a mixture of E,Z-4-[2-methyl-2-(6-propyl-1,1,4,4- tetramethyl-1,2,3,4-tetrahydronapth-7-yl)-vinyl]-benzoic acid 4-hydroxyanilides as a colorless oil. The oil was suspended in methanol producing colorless needles. Recrystallization from 50% EtOH/50% water afforded a white precipitate at 30% yield, which was purified by preparative HPLC using an octadecylsilane 212×250 mm column. Analytical HPLC was also used including a octadecylsilane 4.6×250 mm column, $CH_3OH$/water at 85:15, UV at 310 nm, flow rate at 1.0 mL/min, and $t_r$=21 min. The structure was confirmed using COSY, HMQC, and NOE diff. The characterization data is as follows: $^1$H-NMR (300 MHz, $(CD_3)_2CO$), 0.93 (t, 3H, J=7.4 Hz), δ 1.27 (s, 6H), 1.28 (s, 6H), 1.62 (m, 2H), 1.69 (s, 4H), 2.21 (d, 3H), 2.59 (m, 2H), 6.40 (s, 1H), 7.13 (s, 1H), 7.2 (s, 1H), 7.24 (AB, 4H, $J_{AB}$=8.69 Hz), 7.76 (AB, 4H, $J_{AB}$=8.32 Hz), 8.23 (s, OH), 9.35 (s, NH).

4-Hydroxyphenylacetic acid (compound 13) and 4-methoxyphenylacetic acid (compound 19) are commercially available from the Aldrich Chemical Company of Milwaukee, Wis.

Methyl 4-hydroxyphenylacetate (compound 14) was prepared as follows. Compound 13 was esterified in methanol with sulfuric acid to produce compound 14 at a quantitative yield. Properties of the product matched those reported in Kuchar M et al., *Collection of Czechoslovak Chemical Communications*, 42:1723 (1977).

Methyl 4-isopropoxyphenylacetate (compound 15) was synthesized by treating 3 g of compound 14 with 2.36 g of 2-bromopropane and 1.66 g of potassium carbonate in DMF at a 60% yield. $^1$H-NMR (300 MHz, $CDCl_3$), δ 1.30 (d; 6H, J=6 Hz), 3.54 (s, 2H), 3.66 (s, 3H), 4.50 (sept. 1H, J=6 Hz), 7.00 (AB, 4H, $J_{AB}$=8.78 Hz).

Methyl 4-benzyloxyphenylacetate (compound 16) was synthesized by treating 2.47 g of compound 14 with 3.82 g of benzyl bromide and 4.11 g of potassium carbonate in DMF at 48% yield. The characterizations data included: 1H-NMR (300 MHz, $CDCl_3$), δ 3.55 (s, 2H), 3.67 (s, 3H), 5.04 (s, 2H), 7.05 (AB, 4H, $J_{AB}$=8.6 Hz), 7.28-7.43 (m, 5H).

4-Isopropoxyphenylacetic acid (compound 17) was synthesized by hydrolyzing compound 15 in 6M aqueous KOH to produce compound 17 as colorless needles at a 92% yield from 90% hexane/10% ethyl acetate. Its properties matched those reported in G Solladie et al., *Tetrahedron*, 59:3315 (2003).

A general method of synthesis is disclosed in PCT Publication No. WO/99/02509 (1999) which is incorporated herein by reference, whereby conventional modifications may be employed to make the following compounds:

E-4-[2-methyl-2-(1,1,4,4-tetramethyl-1,2,3,4-tetrahydronaphth-7-yl)-vinyl]-phenyl-2'-(4'methoxyphenyl)-1'-ethanone (compound 20), E-4-[2-methyl-2-(1,1,4,4-tetramethyl-1,2,3,4-tetrahydronaphth-7-yl)-vinyl]-phenyl-2'-(4'-isopropoxyphenyl)-1'-ethanone (compound 21), and, E-4-[2-methyl-2-(1,1,4,4-tetramethyl-1,2,3,4-tetrahydronaphth-7-yl)-vinyl]-phenyl-2'-(4'-benzyloxyphenyl)-1'-ethanone (compound 22).

A solution of 1.25 equivalents of 4-substituted phenylacetic acid in dry tetrahydrofuran ("THF") was slowly added with stirring to 2.45 equivalents of 2M lithium diisopropylamide in THF at room temperature. The reaction mixture was stirred at room temperature for 1.5 hours and then slowly added with stirring to a solution of 1.0 equivalent of compound 5 in THF at room temperature. The reaction was stirred at room temperature overnight and then slowly added with stirring to 6M hydrochloric acid at room temperature. The organic phase was separated and washed using 1.2 M aqueous sodium carbonate and water and then concentrated to ⅕ volume. The hot solution was diluted with 5 volumes of isopropanol. The mixture was cooled to 0° C., and the product was collected by filtration and washed using cold isopropanol to produce compound 20 in the form of colorless needles (from acetic acid) at a 30% yield. The structure was confirmed by COSY and HMQC. HPLC using octadecylsilane 4.6×250 mm column, $CH_3OH$/water 85:15, UV 310 nm, flow rate 1.0 mL/min., and at $t_r$=39 min: $^1$H-NMR (400 MHz, $(CD_3)_2SO$), δ 1.23 (s, 6H), 1.27 (s, 6H), 1.63 (s, 4H), 2.24 (s, 3H), 3.70 (s, 3H), 4.29 (s, 2H), 6.84 (s, 1H), 7.02 (AB, 4H, $J_{AB}$=8.69 Hz), 7.31 (s, 2H), 7.46 (s, 1H), 7.78 (AB, 4H, $J_{AB}$=8.32 Hz); $^{13}$C-NMR (75 MHz, $(CD_3)_2SO$), δ 18 ($C_{31}$), 32.2 ($C_{27}$, $C_{28}$, $C_{29}$, $C_{30}$), 34.2 ($C_2$, $C_3$), 35 ($C_1$, $C_4$), 44.1 ($C_{20}$), 55.7 ($C_{32}$), 125.4 ($C_{12}$), 158 ($C_{11}$), 197 ($C_{19}$), 114.2, 123.8, 124.2, 127, 127.5, 128.7, 129.4, 130.9, 134.4, 139.8, 140.3, 143, 144.2, 144.6 ($C_{ar}$).

Compound 21 was produced as colorless needles from acetic acid at a 43% yield. HPLC confirmed the identity (octadecylsilane 4.6×250 mm column, $CH_3OH$/water 85:15, UV 310 nm and flow rate 1.0 mL/min) at $t_r$=49 min.: $^1$H-NMR (400 MHz, $(CD_3)_2SO$), δ 1.21 (d, 6H, J=6 Hz), 1.23 (s, 6H), 1.26 (s, 6H), 2.25 (s, 3H), 4.22 (s, 2H), 4.51 (sept. 1H, J=6 Hz), 6.84 (s, 1H), 6.98 (AB, 4H, J=8.67 Hz), 7.29 (s, 2H), 7.49 (s, 1H), 7.75 (AB, 4H, J=8.42 Hz); $^{13}$C-NMR (75 MHz, $(CD_3)_2SO$), δ 17.9 ($C_{31}$), 32.1 ($C_{27}$, $C_{28}$, $C_{29}$, $C_{30}$, $C_{33}$, $C_{34}$), 34.8 ($C_2$, $C_3$), 35.9 ($C_1$, $C_4$), 44.9 ($C_{20}$), 70.2 ($C_{32}$), 127 ($C_{12}$), 157.8 ($C_{11}$), 197 ($C_{19}$), 116.5, 124.2, 124.8, 126.6, 127.3, 129.3, 130.1, 131.4, 135.5, 140.7, 141.6, 144.1, 145.1, 145.3 ($C_{ar}$).

Compound 22 was a white powder from acetic acid produced at a 60% yield. HPLC (octadecylsilane 4.6×250 mm column, $CH_3OH$/water 85:15, UV 310 nm and flow rate 1.0 mL/min. $t_r$=66 min.): $^1$H-NMR (400 MHz, $(CD_3)_2SO$), δ 1.18 (s, 6H), 1.21 (s, 6H), 1.58 (s, 4H), 2.18 (s, 3H), 4.23 (s, 2H), 5.00 (s 2H), 6.80 (s, 1H), 7.00 (AB, 4H, $J_{AB}$=8.42 Hz), 7.25-7.42 (m, total of 8H), 7.72 (AB, 4H, $J_{AB}$=8.23 Hz); $^{13}$C-NMR (75 MHz, $(CD_3)_2SO$), δ 17 ($C_{38}$), 31.9 ($C_{34}$, $C_{35}$, $C_{36}$, $C_{37}$), 34.2 ($C_2$, $C_3$), 34.2 ($C_2$, $C_3$), 34.9 ($C_1$, $C_4$), 44.1 ($C_{20}$), 69 ($C_{27}$), 123.9 ($C_{12}$), 157.3 ($C_{11}$), 197.9 ($C_{19}$), 115.1, 123.5, 125.9, 126.8, 127.6, 127.9, 128, 128.7, 128.9, 129.5, 130.9, 134.3, 137.4, 139.7, 140.4, 143, 144.2, 144.5 ($C_{ar}$).

E-4-[2-methyl-2-(1,1,4,4-tetramethyl-1,2,3,4-tetrahydronapth-7-yl)-vinyl]-phenyl-2'-(4'-hydroxyphenyl)-1'-ethanone (compound 23) was synthesized by stirring a solution of 0.46 g (0.965 mmol) of compound 21 in 20 mL of dry $CH_2C_{12}$ at –20° C. To that solution, 0.28 g (2.413 mmol) of $BCl_3$ was added drop wise. The reaction mixture was warmed to room temperature and stirred for 30 minutes. The mixture was then poured into ice water, saturated with NaCl, and extracted with 30 mL of diethyl ether. The organic layer was dried over $Na_2SO_4$ and concentrated to 5 mL. The formed precipitate was filtered off and dried to produce compound 23 as colorless needles from acetic acid. The structure of compound 23 was confirmed using COSY, HMQC and NOE diff. HPLC (octadecylsilane 4.6×250 mm column, $CH_3OH$/water 85:15, UV 310 nm, flow rate 1.0 mL/min., $t_r$=22 min.); $UV_{max}$ (DMSO), 322.5 (52 100); $^1$H-NMR (400 MHz, $(CD_3)_2CO$), δ1.29 (s, 6H), 1.33 (s, 6H), 1.72 (s, 4H), 2.31 (s, 3H), 4.26 (s, 2H), 6.90 (s, 1H), 6.98 (AB, 4H, $J_{AB}$=8.50 Hz), 7.35 (s, 2H), 7.56 (s, 1H), 7.81 (AB, 4H, $J_{AB}$=8.34 Hz); OH exchanges with water from the solvent; $^{13}$C-NMR (75 MHz, $(CD_3)_2CO$), δ 18.1 ($C_{31}$), 32.3 ($C_{27}$, $C_{28}$, $C_{29}$, $C_{30}$), 35.2 ($C_2$, $C_3$), 36.2 ($C_1$, $C_4$), 45.3 ($C_{20}$), 127.2 ($C_{12}$), 157.2 ($C_{11}$), 198 ($C_{19}$), 116.3, 124.6, 125.2, 126.8, 127.7, 129.7, 130.3, 131.7, 135.9, 139.9, 141.9, 144.2, 145.3, 145.7 ($C_{ar}$).

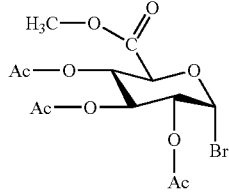

(Compound 24)

The structure of bromo compound 24 is shown above, which was synthesized using a known procedure. (See Bollenback G N et al., *J Am Chem Soc*, 77:3310 (1955)).

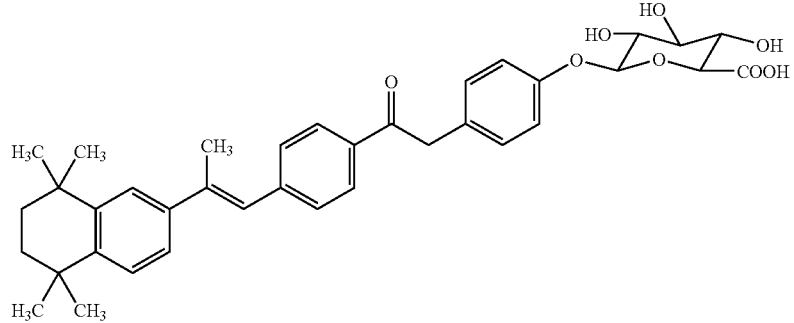

(Compound 25)

Compound 25 was synthesized from compounds 23 and 24 by first reacting with silver oxide and then reacting with potassium carbonate and methanol. Then, the reaction products are treated with sodium hydroxide in a mixture of methanol and water producing compound 25.

2,3,4,6-Tetra-O-(methoxymethyl)-D-gluconic acid-δ-lactone (compound 26.2) was synthesized as follows. To a flame dried flask under argon atmosphere, 7.38 g (41.4 mmol) of δ-gluconolactone (compound 26.1) was combined with 400 mL $CH_2Cl_2$. Compound 26.1 is available from Sigma-Aldrich, St. Louis, Mo. Upon cooling the suspension using an ice bath, diisopropylethylamine (57.6 mL, 331 mmol) was added drop wise. Then, chloromethyl methyl ether (50 g, 621 mmol) was carefully added via an addition funnel. A significant amount of white smoke formed in the reaction vessel. Solid tetrabutylammonium iodide (50 g, 134 mmol) was added, and the solution was allowed to warm to room temperature. The reaction was stirred in darkness for 48 hours, and the solution gradually turned red in color. After cooling the vessel to 0° C., saturated aqueous $NH_4Cl$ (75 mL) was added. Then, the mixture was diluted with brine, and the combined aqueous layers were extracted with $CH_2Cl_2$ (3×). The combined organic layers were dried over $MgSO_4$, filtered and concentrated. Then, the solids were titrated using ether (4×), and the ether was concentrated. The resultant oil was chromatographed on silica gel (1:1 hexanes/ethyl acetate) to afford 12.04 g (83% yield) of clear oil. $[\alpha]_D$ 118.4 (c 2.15, $CH_2Cl_2$); IR ($cm^{-1}$) 2948 (s), 2885 (s), 1757 (s), 1464 (m), 1443 (m), 1213 (s), 1150 (s), 1035 (s), 912 (m), $^1H$ NMR ($CDCl_3$) 3.36-3.42 (m, 12H), 3.77 (dd, 1H, J=3.8, 11.3 Hz), 3.82 (dd, 1H, J=2.8, 11.3 Hz), 3.99-4.05 (m, 2H), 4.29 (d, 1H, J=6.6 Hz), 4.55-4.56 (m, 1H, 4.65 (s, 2H), 4.69-4.92 (m, 7H), $^{13}C$ NMR ($CDCl_3$) δ 55.42, 56.05, 56.11, 56.22, 66.12, 73.69, 74.77, 78.43, 96.56, 96.66, 96.78, 96.91, 97.13, 168.70; HRMS (ES) calcd for $C_{14}H_{26}O_{10}$ (M+Na) 377.1424, found 377.1408.

Preparation of dimethyl titanocene $Cp_2Ti(CH_3)_2$ (Petasis' reagent). To a flame dried flask under argon atmosphere was added titanocene dichloride (14.63 g, 58.8 mmol) and absolute ether (300 mL), which was cooled to 10° C. Methyl lithium (100 mL, 140 mmol, 1.4 M) was carefully added drop wise via an addition funnel under darkness. The cold bath was removed, and the red solution was allowed to stir for 10 min. The solution was cooled to 0° C., and ice water (25 mL) was carefully added to quench the unreacted methyl lithium. The layers were separated, and the aqueous layer was extracted using ether (2×). The combined organic layers were dried over $Na_2SO_4$ under argon for 1 hour and concentrated in darkness at 20° C. to produce 12.4 g of orange solid. Dry toluene (100 mL) was added, and the reagent was stored at 4° C. and used without characterization.

Preparation of 2,6-anhydro-1-deoxy-3,4,5,7-tetra-O-(methoxymethyl)-D-gluco-hept-1-enitol (compound 26.3). To a flame dried flask under argon atmosphere was added the sugar lactone compound 26.2 (10.05 g, 28.4 mmol) and dissolved in dry toluene (140 mL) via an addition funnel. The toluene solution of dimethyl titanocene (12.4 g, 59 mmol) was added drop wise via an addition funnel to produce a red solution. The flask was equipped with a reflux condenser and heated to 70° C. and stirred in darkness for 18 hours. The resultant black solution was cooled and poured into hexanes (~500 mL). The formed precipitate was filtered through Celite. The supernatant was concentrated yielding a red oil that was chromatographed on silica gel (4:1 then 2:1 hexanes/ethyl acetate) producing 8.66 g (87% yield) of yellowish oil. $[\alpha]_D$ 46.8 (c 2.33, $CH_2Cl_2$); IR ($cm^{-1}$) 2940 (m), 2895 (m), 1750 (w), 1440 (w), 1154 (s), 1032 (s), 918 (m), $^1H$ NMR (DMK-$d_6$) 63.31-3.37 (m, 12H), 3.64-3.71 (m, 2H), 3.78-3.83 (m, 2H), 3.88-3.89 (m, 1H) 4.12 (d, 1H, J=5.4 Hz), 4.35 (s, 1H), 4.51 (s, 1H), 4.62 (s, 2H), 4.66-4.84 (m, 6H), $^{13}C$ NMR (DMK-$d_6$) δ 55.15, 55.87, 56.04, 56.19, 67.50, 75.42, 76.68, 77.36, 81.08, 93.43, 95.35, 97.23, 97.64, 97.81, 156.39; HRMS (ES) calculated for $C_{15}H_{28}O_9$ (M+Na) 375.1631, found 375.1628.

Preparation of 2,6-anhydro-1-deoxy-1-[4-(hydroxymethyl)-phenyl]-3,4,5,7-tetra-O-(methoxymethyl)-D-glycero-D-gulo-heptitol (compound 26.4). To a flame dried flask under argon atmosphere was added the exocyclic olefin (compound 26.3) (3.75 g, 10.6 mmol) dissolved in dry THF (100 mL). 9-Borabicyclo[3.3.1]nonane (53.2 mL, 26.6 mmol, 0.5

M) was added via addition funnel. The flask was equipped with a reflux condenser, heated to 75-80° C., and refluxed for 4.5 hours. The mixture was cooled to room temperature, then $K_3PO_4$ (10 mL, 3 M) was added, and the reaction was allowed to stir for 10 minutes. p-Bromobenzyl alcohol (3.98 g, 21.3 mmol) and $PdCl_2$ (dppf) (0.686 g, 0.85 mmol) dissolved in DMF (100 mL) were added via addition funnel. The reaction was stirred for 18 hours. The reaction was diluted with water and ether. The layers were separated. The organic layer was washed with water and brine. The combined aqueous layers were extracted with ether (3×). The organic layers were combined, dried over $MgSO_4$, concentrated, and chromatographed (1:1 then 1:2 hexanes/ethyl acetate) to produce 3.29 g (67% yield) of orange oil. $[\alpha]_D$ −26.2 (c 1.15, DMK); IR (cm$^{-1}$) 3470 (w), 2932 (m), 2887 (m), 1692 (m), 1444 (w), 1150 (s), 1101 (s), 1024 (s), 918 (m); $^1$H NMR (DMK-d$_6$) δ 2.60 (dd, 1H, J=9.4, 14.4 Hz), 3.18-3.42 (m, 5H), 3.25 (s, 3H), 3.35 (s, 3H) 3.40 (s, 3H), 3.44 (s, 3H), 3.54-3.61 (m, 2H), 3.73 (dd, 1H, J=1.8, 11.3 Hz), 4.51-4.58 (m, 4H), 4.70 (d, 1H, J=6.5 Hz), 4.77-4.85 (m, 4H), 4.93 (d, 1H, J=6.5 Hz), 7.25 (s, 4H); $^{13}$C NMR (DMK-d$_6$) δ 38.35, 55.04, 56.45, 56.55, 64.44, 64.57, 67.42, 77.97, 79.07, 80.32, 81.63, 84.83, 97.20, 99.01, 99.19, 99.32, 127.15, 130.11, 138.75, 141.03; HRMS (ES) calculated for $Ca_{22}H_{36}O_{10}$ (M+Na) 483.2206, found 483.2188.

Preparation of 2,6-anhydro-1-deoxy-1-[4-(methoxymethyl)phenyl]-3,4,5,7-tetra-O-(methoxymethyl)-D-glycero-D-gulo-heptitol (compound 26.5). To a flame dried flask under argon atmosphere was added compound 26.4 (2.44 g, 5.3 mmol)(C-glycoside benzyl alcohol) dissolved in dry THF (100 mL). Sodium hydride (0.63 g, 26.5 mmol) was added to the flask, and the suspension was stirred for 1.5 hours. Iodomethane (4.5 g, 31.7 mmol) dissolved in THF (10 mL) was cannulated into the reaction mixture, and the reaction was stirred for 18 hours. After cooling in an ice bath, water was carefully added to quench excess NaH. The mixture was extracted using ether (3×), and the organic layers were combined, washed, dried over $MgSO_4$, concentrated, and then chromatographed (1:1 then 1:2 hexanes/ethyl acetate) to produce 2.37 g (94% yield) of clear oil. $[\alpha]_D$ −27.0 (c 4.70, DMK); IR(cm$^{-1}$) 2981 (s), 2883 (s), 1701 (w), 1513 (m), 1444 (m), 1378 (m), 1301 (m), 1158 (s), 1105 (s), 1028 (s), 918 (s); $^1$H NMR (DMK-d$_6$) δ 2.61 (dd, 1H, J=9.4, 14.4 Hz), 3.19-3.42 (m, 5H), 3.24 (s, 3H), 3.30 (s, 3H) 3.35 (s, 3H), 3.40 (s, 3H), 3.44 (s, 3H), 3.54-3.64 (m, 2H), 3.73 (dd, 1H, J=2.6, 13.5 Hz), 4.38 (s, 2H), 4.50 (d, 1H, J=6.4 Hz), 4.54 (d, 1H, J=6.4 Hz), 4.70 (d, 1H, J=6.5 Hz), 4.77-4.85 (m, 4H), 4.93 (d, 1H, J=6.5 Hz), 7.21 (d, 2H, J=8.0 Hz), 7.28 (d, 2H, J=8.0 Hz); $^{13}$C NMR (DMK-d$_6$) δ 33.39, 55.05, 56.47, 56.49, 56.57, 57.97, 67.46, 74.84, 78.00, 79.10, 80.23, 81.66, 84.86, 97.20, 99.01, 99.21, 99.32, 128.15, 130.19, 137.23, 139.45; HRMS (ES) calculated for $Ca_{23}H_{38}O_{10}$ (M+Na) 497.2363, found 497.2384.

Preparation of 2,6-anhydro-7-deoxy-7-[4-(methoxymethyl)phenyl]-3,4,5-tri-O-acetyl-L-glycero-L-gulo-heptinoic acid methyl ester (compound 26.6). The MOM-protected glucoside compound 26.5 (2.43 g, 5.12 mmol) was dissolved in methanol (500 mL) and placed in a flask at room temperature. Aqueous HCl (6 N, 26 mL) was added, and the solution was stirred for 18 hours. Then, the mixture was concentrated to dryness. In a separate flask, KBr (2.42 g, 20.38 mmol) and TEMPO (3.19 g, 20.41 mmol) were added to saturated $NaHCO_3$ solution (400 mL) and stirred for 20 minutes at 0° C. Aqueous NaOCl (11.2 mL, 1.6-2.0 M) was added, and the mixture was stirred for 10 minutes. The deprotected sugar (formed by reacting the MOM-protected sugar compound 26.5 with HCl in methanol as described above) was dissolved in saturated $NaHCO_3$ solution (100 mL) and added to the flask containing the TEMPO mixture. That new total mixture was stirred for 45 minutes at 0° C. The reaction was quenched using EtOH (50 mL), and the reaction mixture was washed with ether in a separatory funnel. The aqueous layer was concentrated to dryness, and the remaining solid was exhaustively triturated with methanol. The methanol was concentrated and dried. The dried residue was suspended in DMF (180 mL). Iodomethane (6.4 g) dissolved in DMF (10 mL) was added, and the reaction mixture was stirred for 20 hours under argon at room temperature. The reaction mixture was supplemented with acetic anhydride (40 mL), pyridine (20 mL), and DMAP (15 mg) and stirred for 18 hours. The reaction mixture was diluted with water and extracted using ethyl acetate (3×). The organic layers were washed using water and brine, and the resultant was dried over $MgSO_4$, concentrated, and chromatographed (2:1 then 1:1 hexanes/ethyl acetate) to produce 1.90 g (82% yield) of compound 26.6 as a clear oil that solidified upon standing. m.p.=84-86° C. $[\alpha]_D$ −13.04 (c 1.15, DMK); IR (cm$^{-1}$) 2956 (w), 2818 (w), 1750 (s), 1440 (m), 1370 (m), 1211 (s), 1105 (m), 1028 (m); $^1$H NMR DMK-d$_6$) δ 1.94 (s, 3H), 1.94 (s, 3H), 1.95 (s, 3H), 2.74-2.81 (m, 1H), 2.90 (dd, 1H, J=3.4, 7.3 Hz), 3.30 (s, 3H), 3.65 (s, 3H), 3.94-3.99 (m, 1H), 4.18 (d, 1H, J=9.8 Hz), 4.38 (s, 2H), 4.90 (t, 1H, J=9.8 Hz), 5.05 (t, 1H, J=9.8 Hz), 5.29 (t, 1H, J=9.8 Hz), 7.22 (s, 4H); $^{13}$C NMR (DMK-d$_6$) δ 20.39, 20.52, 20.60, 38.12, 52.67, 58.03, 70.62, 72.53, 74.09, 74.73, 76.41, 78.62, 128.25, 130.16, 137.43, 137.76, 168.40, 169.89, 170.07, 170.30; HRMS (ES) calculated for $Ca_2H_{28}O_{10}$ (M+Na) 475.1580, found 475.1577.

Preparation of 2,6-anhydro-7-deoxy-7-[4-(bromomethyl)phenyl]-3,4,5-tri-O-acetyl-L-glycero-L-gulo-heptinoic acid methyl ester (compound 26.7). To a dry flask equipped with a $CaSO_4$ drying tube was added the C-glucuronide methyl ether compound 26.6 (462 mg, 1.02 mmol) along with 30% HBr in acetic acid (5 mL, 25 mmol) at 0° C. The mixture was stirred for 30 minutes at 0° C., warmed to room temperature, and stirred for 18 hours. The mixture was diluted with methylene chloride and carefully washed with water and a saturated solution of $NaHCO_3$. The organic layer was dried over $MgSO_4$, concentrated, and chromatographed (2:1 then 1:1 hexanes/ethyl acetate) to produce 440 mg (86% yield) of white foam that was crystallized using ether; m.p.=116-117° C. $[\alpha]_D$ −12.03 (c 5.57; DMK); IR (cm$^{-1}$) 3026 (w), 2952 (w), 1754 (s), 1440 (m), 1370 (m), 1215 (s), 1101 (m), 1036 (m); $^1$H NMR DMK-d$_6$) δ 1.93 (s, 3H), 1.94 (s, 3H), 1.95 (s, 3H), 2.76-2.83 (m, 1H), 2.92 (dd, 1H, J=3.5, 7.3 Hz), 3.64 (s, 3H), 3.96-3.99 (m, 1H), 4.20 (d, 1H, J=9.7 Hz), 4.62 (s, 2H), 4.90 (t, 1H, J=9.7 Hz), 5.05 (t, 1H, J=9.7 Hz), 5.29 (t, 1H, J=9.7 Hz), 7.25 (d, 2H, J=8.2 Hz), 7.36 (d, 2H, J=8.2 Hz); $^{13}$C NMR (DMK-d$_6$) δ 20.40, 20.52, 20.63, 34.37, 38.12, 52.69, 70.58, 72.52, 74.04, 76.35, 78.43, 129.88, 130.68, 137.26, 138.67, 168.39, 169.91, 170.09, 170.29; HRMS (ES) calculated for $C_{21}H_{25}BrO_9$ (M+Na) 523.0580, found 523.0602.

Preparation of 2,6-anhydro-1-deoxy-1-[4-(methoxymethyl)phenyl]-3,4,5,7-tetra-O-acetyl-D-glycero-D-galo-heptitol (compound 26.8). The MOM-protected glucoside compound 26.5 (0.643 g, 1.35 mmol) was dissolved in methanol (34 mL) and placed in a flask at room temperature. Aqueous HCl (6 N, 6.7 mL) was added, and the solution was stirred for 18 hours. The mixture was concentrated to dryness. Acetic anhydride (4 mL) and pyridine (3 mL) were added to the paste along with a catalytic amount of DMAP, and the mixture was stirred for 18 hours at room temperature. The reaction mixture was diluted with water and extracted with ethyl acetate (3×). The organic layers were combined, washed with water and brine, dried over $MgSO_4$, filtered, concentrated, and chromatographed (1:1 hexanes/ethyl acetate) to produce 570 mg (90% yield) of compound 26.8 in the form of a white solid, m.p.=120-122° C. $[\alpha]_D$ −4.0 (c 0.78, DMK); IR (cm$^{-1}$) 2940 (w), 2862 (w), 1750 (s), 1436 (w), 1370 (m), 1224 (s), 1105 (m), 1032 (m); $^1$H NMR CDCl$_3$ δ 1.96-2.02 (m, 12H), 2.78 (s, 2H, J=5.8 Hz), 3.36 (s, 3H), 3.52-3.57 (m, 2H), 4.02 (dd, 1H, J=2.3, 12.2 Hz), 4.20 (dd, 1H, J=5.3, 12.2 Hz), 4.40 (s, 2H), 4.92 (t, 1H, J=9.6 Hz), 5.03 (t, 1H, J=9.6 Hz), 5.15 (t, 1H, J=9.6 Hz), 7.16 (d, 2H, J=8.0 Hz), 7.23 (d, 2H, J=8.0 Hz); $^{13}$C NMR (DMK-$d_6$) δ 20.55, 20.57, 20.65, 38.08, 58.02, 63.05, 69.70, 72.81, 74.76, 74.86, 76.05, 78.60, 128.20, 130.21, 137,65, 137.75, 170.04, 170.16, 170.37, 170.59; HRMS (ES) calculated for $C_{23}H_{30}O_{10}$ (M+Na) 489.1737, found 489.1727.

Preparation of 2,6-anhydro-1-deoxy-[4-(bromomethyl)phenyl]-3,4,5,7-tetra-O-acetyl-1)-glycero-D-gulo-heptitol (compound 26.9). To a dry flask equipped with a drying tube was added the C-glycoside methyl ether compound 26.8 (0.54 g, 1.16 mmol) along with 30% HBr in acetic acid (5 mL, 25 mmol) at 0° C. The mixture was stirred for 30 minutes at 0° C. The mixture was then stirred for 18 hours at room temperature. The mixture was diluted with methylene chloride and carefully washed with water and saturated NaHCO$_3$ solution. The organic layer was dried over MgSO$_4$, concentrated and chromatographed (2:1 then 1:1 hexanes/ethyl acetate) to produce 593 mg (97% yield) of compound 26.9 as a white solid, m.p.=141-142° C. $[\alpha]_D$ -4.67 (c 2.57, DMK); IR (cm$^-$) 2993 (w), 2952 (w), 1754 (s), 1440 (w), 1374 (m), 1224 (s), 1105 (w), 1052 (m); $^1$H NMR (DMK-$d_6$) δ 1.92-1.98 (m, 12H), 2.72 (dd, 1H, J=7.3, 8.6 Hz), 2.88 (dd, 1H, J=3.2, 7.3 Hz), 3.77-3.85 (m, 2H), 4.00 (dd, 1H, J=2.4, 6.1 Hz), 4.21 (dd, 1H, J=5.9, 6.1 Hz), 4.63(s, 2H), 4.86 (t, 1H, J=9.6 Hz), 4.97 (t, 1H, J=9.6 Hz), 5.22 (t, 1H, J=9.6 Hz), 7.25 (d, 2H, J=8.2 Hz), 7.37 (d, 2H, J=8.2 Hz); $^{13}$C NMR (DMK-$d_6$) δ 20.49, 20.60, 34.32, 38.07, 63.03, 69.73, 72.82, 74.85, 76.07, 78.40, 129.72, 130.68, 137.12, 138.92, 169.97, 170.10, 170.30, 170.52; HRMS (ES) calculated for $C_{22}H_{27}BrO_9$ (M+Na) 537.0736, found 537.0724.

Preparation of aldehyde compound 27. (See FIG. 8). A solution of ethyl ester compound 5 in dry THF was cooled to −78° C. DIBAL (1 equivalent) in dry THF under argon was added to the reaction under argon and stirred for 4 hours. The reaction mixture warmed to room temperature and was stirred for 18 hours. The THF solvent was removed under reduced pressure. The residue was partitioned between ethyl acetate and 2 N HCl. The ethyl acetate layer was washed with brine, dried over Na$_2$SO$_4$, filtered, and concentrated. The solvent was removed. The resulting product was purified using standard purification techniques to produce the aldehyde compound 27.

Preparation of tert-butyl-dimethylsilylcyanohydrin (compound 28) from aldehyde compound 27. A mixture compound 27 (3.62 mmol) in dry CH$_2$Cl$_2$ (50 mL) was added to a flame-dried flask under argon atmosphere. A catalytic amount of Et$_3$N (0.1 mL) was added. Tert-butyldimethylsilyl cyanide (1.0 g. 7.08 mmol) dissolved in CH$_2$Cl$_2$ (10 mL) was added by cannula. The reaction was stirred for 20 hours. Then, the solution was concentrated, chromatographed (95:5 hexanes/ethyl acetate), dried over Na$_2$SO$_4$ under argon, and subjected to vacuum overnight producing compound 28.

Preparation of compound 29. To a flame dried flask under argon atmosphere was added THF (40 mL) along with LiHMDS (1.0 M in hexanes, 3.8 mL, 3.8 mmol). The mixture was cooled to −78° C. Compound 28 (2.54 mmol) in THF (15 mL) was added by cannula into the flask. The solution was stirred for 30 minutes at −78° C. Crystalline bromoglucoronide (compound 26.7) (2.78 g, 5.56 mmol) in THF 15 mL) was cannulated into the flask, and the mixture was stirred for 3 hours at −78° C. The flask was removed from the cold bath and quenched with 1 M NH$_4$Cl (10 mL). The mixture was extracted with ethyl acetate (3×), the organic layers were combined, washed with brine, dried over Na$_2$SO$_4$, filtered, concentrated and chromatographed (2:1 hexanes/ethyl acetate) producing the alkylated product and some recovered compound 26.7. The alkylated product was taken up in 1% aqueous THF (200 mL) and chilled to 0° C. Tetra-n-butylammonium fluoride (309 mg, 1.18 mmol) was added which darkened the solution. The solution was stirred for 1 hour. The reaction mixture was diluted with water and extracted with ethyl acetate (3×). The organic layers were combined, washed with brine, dried over NaSO$_4$, filtered, concentrated, and chromatographed (2:1 hexanes/ethyl acetate) producing the protected methyl ester of compound 29.

The protected methyl ester of compound 29 (1.64 mmol) was dissolved in methanol (500 mL) and added to a flask. The mixture was cooled to 4° C. Potassium carbonate (136 mg, 0.98 mmol) was added to the flask and stirred for 20 hours. The reaction mixture was concentrated to about 200 mL at 25-30° C. Adjustment to the original volume using methanol was followed by adding 1 N KOH (14 mL, 14 mmol). After stirring for 20 hours at 4° C., the reaction mixture was warmed and stirred for 5 hours at room temperature. The reaction mixture was cooled to 0° C. and adjusted to 7 pH using 4 N HCl. The reaction mixture was concentrated to about 100 mL at 25-30° C., cooled to 0° C., and adjusted to 3 pH using 1 N HCl. The suspension was extracted using ethyl acetate. The organic layers were combined, dried over Na$_2$SO$_4$ under argon for 2 hours, and concentrated. The residue was chromatographed on reverse phase silica gel (gradient 70:30 to 85:15 methanol/water) producing compound 29.

Preparation of compound 30. THF (10 mL) and LiHMDS (1.0 M in hexanes, 0.78 mL, 0.78 mmol) were added to a flame dried flask under argon atmosphere. The mixture was cooled to −78° C. Compound 28 (0.51 mmol) in THF (5 mL) was added by cannula into the flask. The solution was stirred for 30 minutes at −78° C. Compound 26.9 (277 mg, 0.53 mmol) in THF (5 mL) was cannulated into the flask. The mixture was stirred for 2 hours at −78° C. The flask was removed from the cold bath and quenched using 1 M NH$_4$Cl (1 mL). The reaction mixture was extracted using ethyl acetate (3×), the organic layers were combined, washed with brine, dried over Na$_2$SO$_4$, filtered, concentrated, and chromatographed (2:1 hexanes/ethyl acetate) producing the alkylated product and some recovered compound 26.9. The alkylated product was taken up in 1% aqueous THF (20 mL) and chilled to 0° C. TBAF (134 mg, 0.51 mmol) was added and the solution darkened. The darkened solution was stirred overnight while warming to room temperature. The reaction mixture was diluted with water and extracted with ethyl acetate (3×). The organic layers were combined, washed with brine, dried over NaSO$_4$, filtered, concentrated, and chromatographed (2:1 hexanes/ethyl acetate) producing the acetate-protected analog of compound 30.

The acetate protected analog of compound 30 (0.18 mmol) was dissolved in methanol (75 mL) and added to a flask. The mixture was cooled to 4° C. Potassium carbonate (25 mg, 0.18 mmol) was added to the flask, and the reaction was stirred for 20 hours. The reaction mixture was cooled to 0° C. and the pH was adjusted to 5 using 1 N HCl. The mixture was extracted using ethyl acetate, and the organic layers were combined, dried over Na$_2$SO$_4$ under argon for 2 hours and concentrated. The residue was chromatographed on reverse phase silica gel (gradient 70:30 to 85:15 methanol/water) to provide compound 30.

Figure 8A:
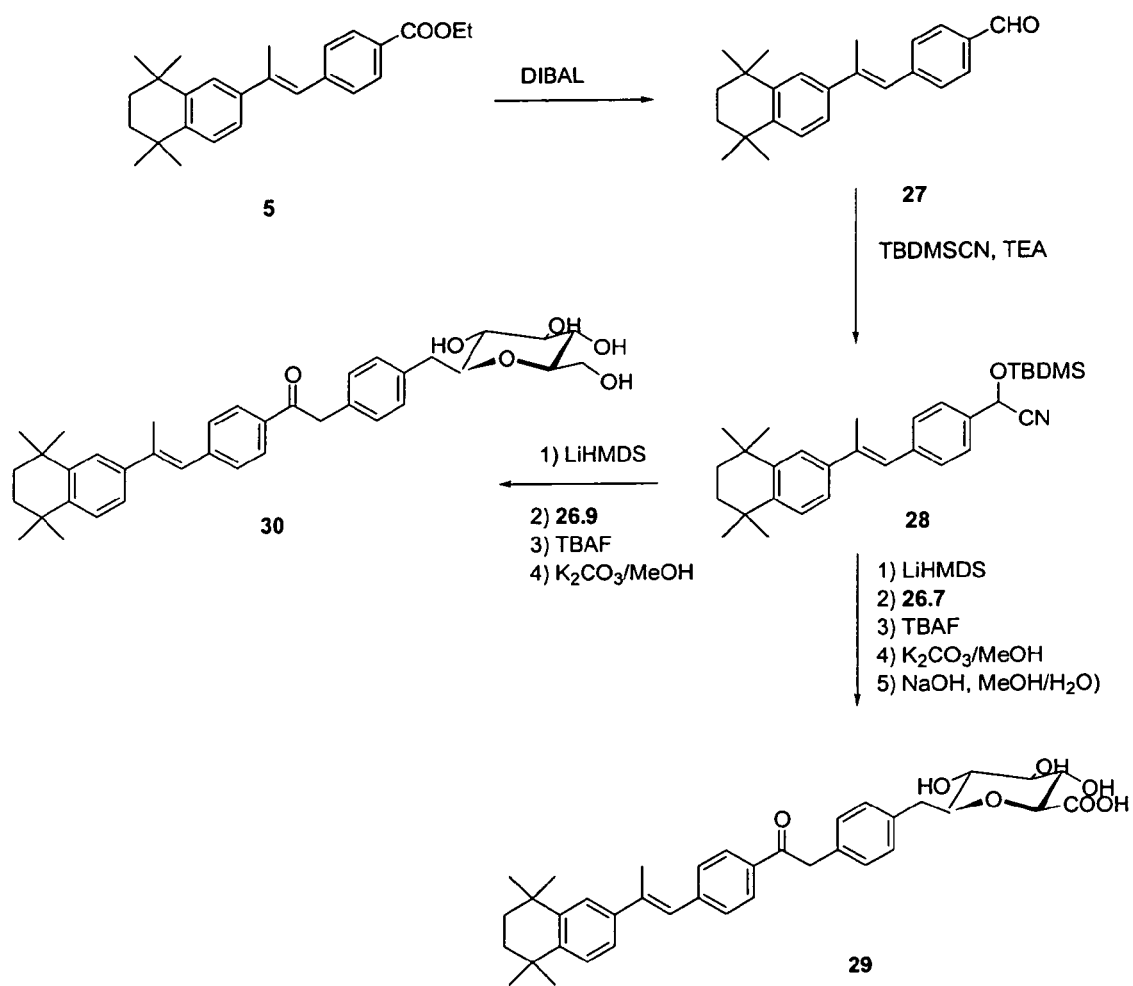
FIG. 8A shows a reaction scheme for another synthesis of $CH_2$-linked sugar analogs of 4-HBTTNPB.
Figure 8B:
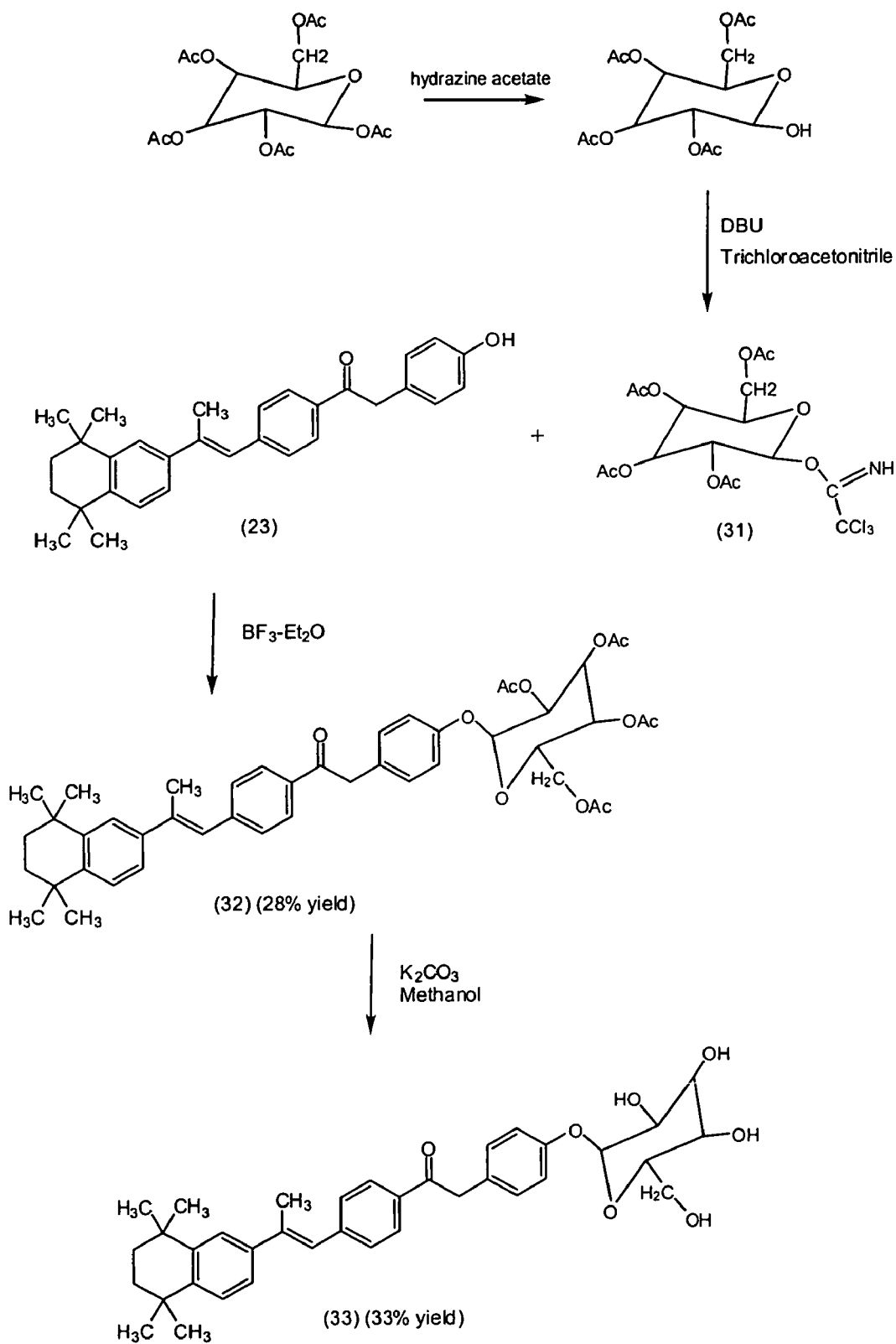
FIG. 8B shows a reaction scheme for the synthesis of another oxygen-linked sugar analog of 4-HBTTNPB.

With reference to the synthetic route shown in FIG. 8B, glycosyl trichloroacetimidate (compound 31) was synthesized according to the procedure set forth in Cheng H et al., *J Med Chem*, 48(2):645 (2005) with a quantitative yield. NMR $^1$H.

Preparation of E-4-[2-methyl-2-(1,1,4,4-tetramethyl-1,2,3,4-tetrahydronaphth-7-yl)-vinyl]-phenyl-2'-(4'-tetra-O-acetyl-beta-D-glucopyranosyloxyphenyl)-1'-ethanone (compound 32). To a solution of 0.14 g (0.319 mmol) of compound 23 in in 10 mL of dry CH$_2$Cl$_2$ were added 0.236 g (0.479 mmol) of compound 31 and 4 Angstrom molecular sieves. The reaction mixture was stirred for 30 min. at room temperature. After cooling to −20° C., 7.85 μL (0.0638 mmol) of BF$_3$Et$_2$O was added and continuously stirred for 2 hours. Molecular sieves were filtered off, and the filtrate was washed with saturated NaHCO$_3$ and brine; and then dried over anhydrous sodium sulfate, filtered, and concentrated. The resultant oil was chromatographed on silica gel (1:1 hexanes/ethyl acetate) producing 0.07 g (28% yield) of white precipitate. NMR $^1$H.

Preparation of E-4-[2-methyl-2-(1,1,4,4-tetramethyl-1,2,3,4-tetrahydronaphth-7-yl)-vinyl]-phenyl-2'-(4'-beta-D-glucopyranosyloxyphenyl)-1'-ethanone (compound 33). To a solution of 0.070 g (0.091 mmol) of compound 32 in 5 mL methanol was added 0.126 g (0.91 mmol) of K$_2$CO$_3$. The reaction mixture was stirred for 18 hours. The reaction mixture was concentrated; and the contents were dissolved in ethyl acetate, washed with water and brine, dried over MgSO$_4$, and concentrated to produce 0.018 g (33% yield) of white precipitate. NMR $^1$H.

Biological Activity

Methods

Nuclear Retinoid Receptor (RAR/RXR) Binding. Competition of retinoids with [$^3$H]-all-trans-RA for binding to RAR$_{alpha}$, RAR$_{beta}$ and RAR$_{gamma}$ and with [$^3$H]-9-cis-RA for binding to RXR$_{gamma}$ was determined using an in vitro ligand binding assay. (See Clagett-Dame et al., Methods for generating and characterizing retinoid receptors from *E. coli* and insect cell expression systems, *Meth. Enzymol.*, 282:13-14 (1997)). Recombinant human RAR$_{alpha}$ was expressed as a fusion protein in *E. coli* (see Repa J J et al., All-trans retinol is a ligand for the retinoic acid receptors, *Proc Natl Acad Sci USA*, 90:7293-7297 (1993)). The human RAR$_{gamma}$ (see Robarge M J et al., N-linked analogs of retinoid O-glucuronides: Potential cancer chemopreventive-chemotherapeutic agents, *Bioorg Med Chem Lett*, 4(17):2117-2122 (1994)), murine RAR$_{beta}$ (see Repa J J et al., All-trans 3,4-didehydroretinoic acid equals all-trans retinoic acid in support of chick neuronal development, *FASEB J*, 10:1078-1084 (1996)) and murine RXR$_{gamma}$ (see Munder M et al., Identification of porcine intestinal accessory factor that enables DNA sequence recognition by vitamin D receptor, *Proc Natl Acad Sci USA*, 92:2795-2799 (1995)) proteins are expressed in insect cells by infection with baculovirus expression vectors followed by the preparation of nuclear extracts. Radiolabeled ligands were added to receptor-containing extracts in the absence and presence of increasing concentrations of competing ligands followed by separating ligand bound to the receptor from that free in solution using a hydroxylapatite (HAP) assay.

Cell growth inhibition and TUNEL assays. MCF-7 breast cancer cells were maintained as described in Chapman J S et al., Hydrolysis of 4-HPR to atRA occurs in vivo but is not required for retinamide-induced apoptosis, *Arch Biochem Biophys*, 419:234-243 (2003). The cells were plated at 50,000 cells/well in 12-well plates. The wells were dosed with varying amounts of retinoid compounds. At cell harvest, propidium iodide was added. Half of the cells were used to determine the number of live and dead cells after adding fluorescein diacetate, which yields a fluorescent product upon cleavage by metabolically active cells. The other half were fixed in 4% paraformaldehyde, dried on aminosilane coated slides and used to determine TUNEL and propidium iodide staining.

Reporter gene assay. The F9-RARE-lacZ reporter cell line (see Wagner M et al., *Development*, 116:55-66 (1992)) was cultured in serum-free L15 medium (15,000 cells/well); dosed with retinoid compounds or vehicle; and assayed for chemiluminescence as described in Chapman J S et al., Hydrolysis of 4-HPR to atRA occurs in vivo but is not required for retinamide-induced apoptosis, *Arch Biochem Biophys*, 419:234-243 (2003). Data were normalized for total protein using the method set forth in Bradford M M, *Anal Biochem*, 72:248-254 (1976).

Assessment of Compound Teratogenicity. Female rats (Harlan Sprague-Dawley, Madison, Wis. approximately 200 to 250 g in weight) were maintained on normal laboratory rat chow and mated with normal rats of the same strain. Pregnant rats were given a single oral bolus dose of compound dissolved in Wesson® corn oil. Each dose was 60-100 μL. The doses were given at day 9.25. Each dose was maintained under standard laboratory conditions until euthanasia at embryonic day 21.5. The fetuses were removed. Fetuses with a heartbeat were determined to be alive. The number of live and dead fetuses were recorded. The number of resorption sites was also recorded. The live fetuses were examined for gross external malformations. All animals were maintained in accordance with protocol approved by the University of Wisconsin-Madison animal care committee.

The teratogenicity data is set forth in Table 1.

TABLE 1

| | Fetal Malformations | | | | |
|---|---|---|---|---|---|
| | Fetuses # (%) | | Gross Malformations # defective/live (%) | | |
| Drug (Litter #) | Live* | Dead & Resorbed | Open Neural Tube | Cleft Palate | Mermaidism |
| | Vehicle | | | | |
| 1 | 13 (93%) | 1 (7%) | 0/13 (0%) | 0/13 (0%) | 0/13 (0%) |
| 2 | 13 (100%) | 0 (0%) | 0/13 (0%) | 0/13 (0%) | 0/13 (0%) |
| | 4HPTTNPB (0.66 micromoles/kg at E9.25) | | | | |
| 3 | 3 (20%) | 12 (80%) | 3/3 (100%) | 3/3 (100%) | 3/3 (100%) |
| 4 | 1 (7%) | 14 (93) | 1/1 (100%) | 1/1 (100%) | 1/1 (100%) |
| 5 | 0 (0%) | 14 (100%) | na** | na | na |

TABLE 1-continued

Fetal Malformations

| Drug (Litter #) | Fetuses # (%) | | Gross Malformations # defective/live (%) | | |
|---|---|---|---|---|---|
| | Live* | Dead & Resorbed | Open Neural Tube | Cleft Palate | Mermaidism |
| 4HBTTNPB (0.66 micromoles/kg at E9.25) | | | | | |
| 6 | 16 (100%) | 0 (0%) | 0/16 (0%) | 0/16 (0%) | 0/16 (0%) |
| 7 | 12 (92%) | 1 (8%) | 0/12 (0%) | 0/12 (0%) | 0/12 (0%) |
| 8 | 14 (100%) | 0 (0%) | 0/14 (0%) | 0/14 (0%) | 0/14 (0%) |
| 9 | 16 (100%) | 0 (0%) | 0/16 (0%) | 0/16 (0%) | 0/16 (0%) |

Figure 9:
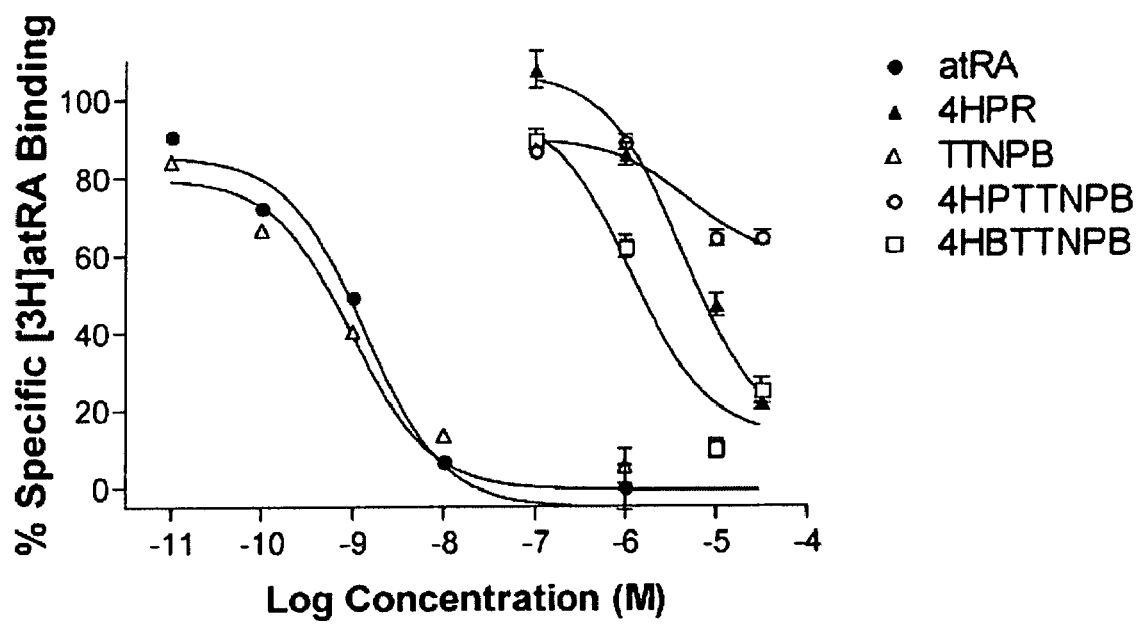
FIG. 9 is a graph comparing the ability of various compounds to interact with the $RAR_{alpha}$ receptor as determined by competition binding assay.
Figure 10:
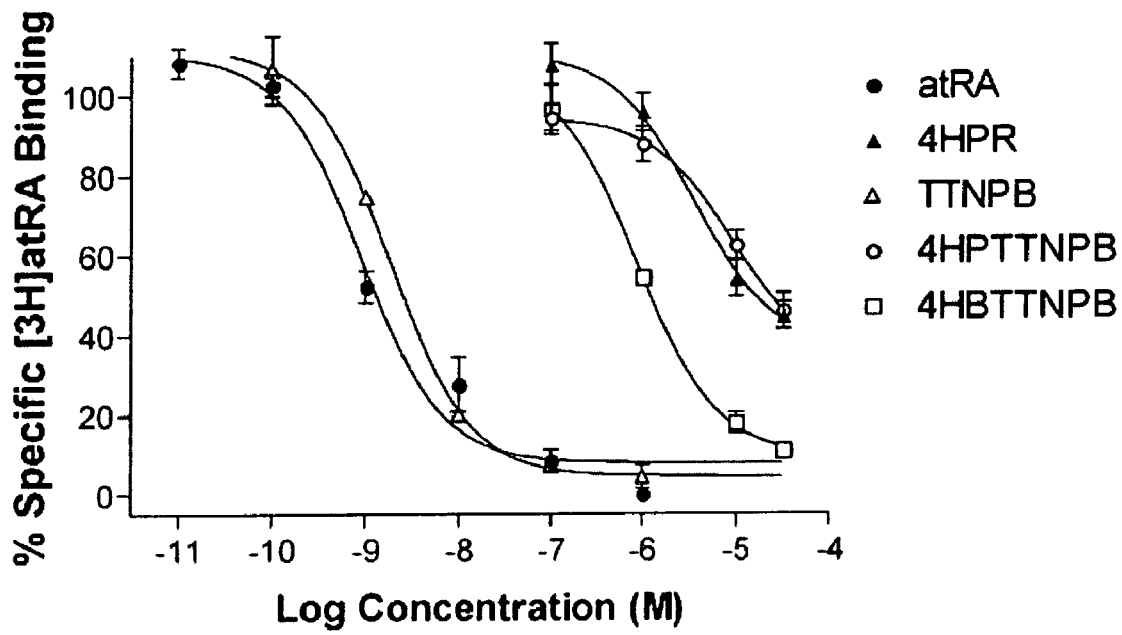
FIG. 10 is a graph comparing the ability of various compounds to interact with the $RAR_{beta}$ receptor as determined by a competition binding assay.
Figure 11:
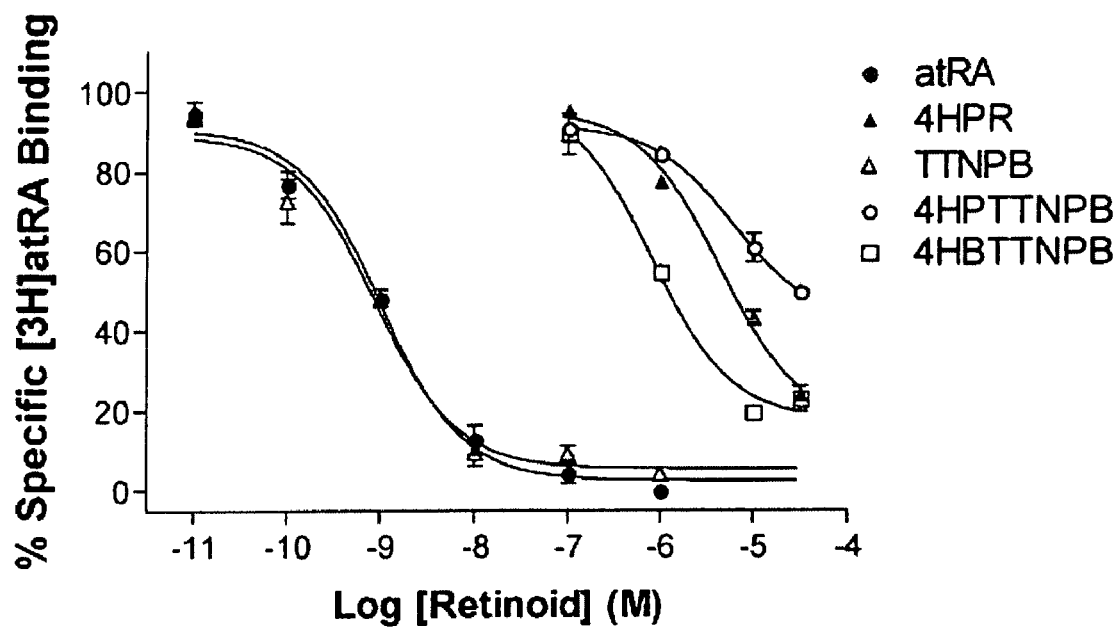
FIG. 11 is a graph comparing the ability of various compounds to interact with the $RAR_{gamma}$ receptor as determined by a competition binding assay.

*Only fetuses that were alive at the time of dissection were scored for gross malformations
**na = not applicable; no fetuses were live at dissection Results Nuclear RAR Binding. The ability of compounds to interact with the retinoic acid receptor types alpha, beta and gamma was tested using a competition binding assay. atRA (all-trans retinoic acid) is commercially available and was obtained from Eastman Kodak (Rochester, N.Y.). TTNPB was very effective at competing with [$^3$H]-all-trans-RA for binding to all of the RARs whereas 4-HPR showed only weak competition (i.e., 3-4 orders of magnitude less potent). Similarly, both 4-HPTTNPB and 4-HBTTNPB competed poorly for [$^3$H]atRA binding to the human RARs. (See FIGS. 9, 10 and 11).

Figure 12:
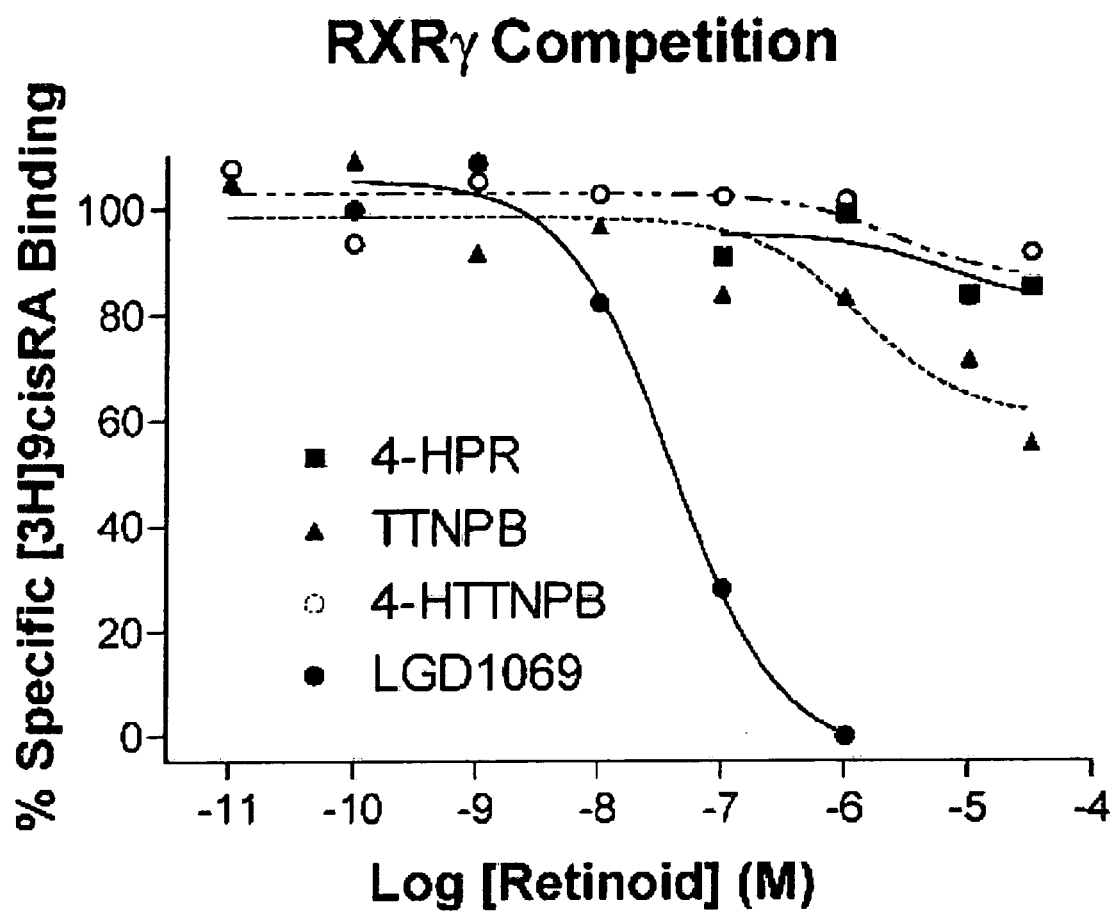
FIG. 12 is a graph comparing the ability of compounds to interact with the $RXR_{gamma}$ receptor as determined using a competition binding assay.

Nuclear RXR Binding. The ability of compounds to interact with the retinoid X receptor type gamma was tested using a competition binding assay. The control synthetic RXR ligand, LGD1069 (see Boehm M F et al., Synthesis and structure-activitiy relationships of novel retinoid X receptor-selective retinoids, *J Med Chem*, 37:2930-2941 (1994)) was very effective at competing with [$^3$H]-9-cis-RA for binding to $RXR_{gamma}$ ($K_i$, 36 nM). TTNPB showed very weak competition at concentrations above $10^{-6}$ M (44% at $10^{-4.5}$ M) whereas 4-HPTTNPB and 4-HPR showed almost no competition with [$^3$H]-9-cis-RA for binding to the human $RXR_{gamma}$ at the highest concentration. (See FIG. 12).

Figure 13:
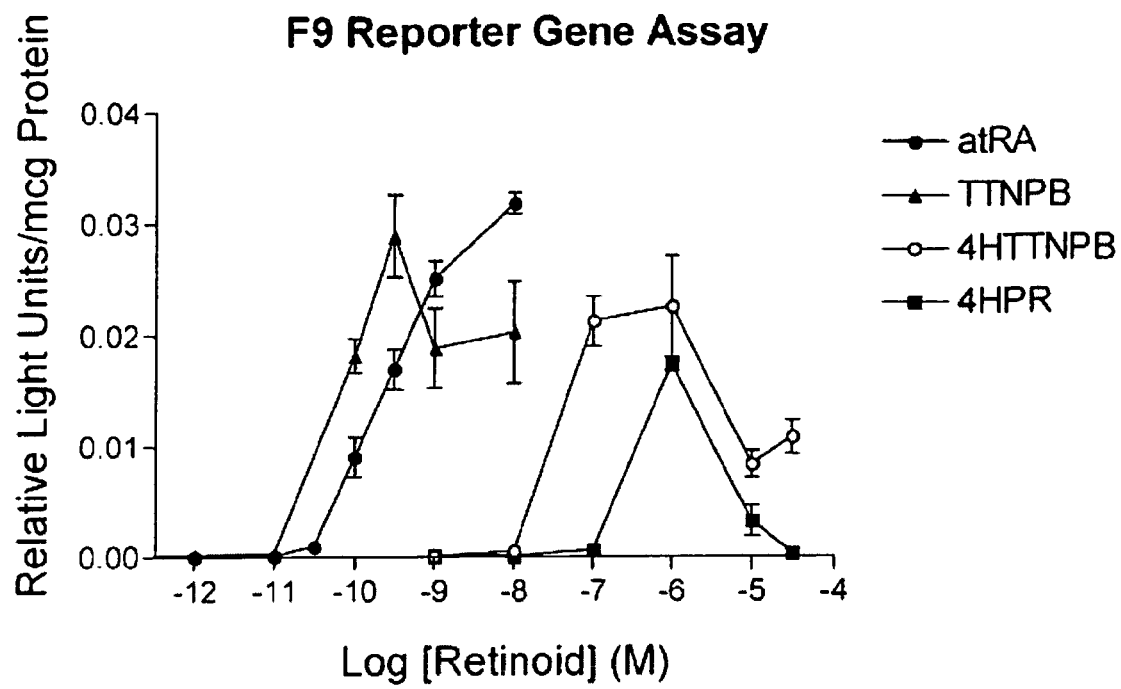
FIG. 13 is a graph of the results obtained in an F9 gene reporter assay plotting the relative light units as a function of the log of the retinoid concentration.

Reporter gene assay. The F9 cell reporter assay yielded β-galactosidase activity in response to exposure of cells to atRA or any compound with similar transactivation potential. That results from ligands binding to the RAR. It also results from activation of β-galactosidase via the retinoid receptor complex binding to the βRARE enhancer (hormone response) element situated upstream of the promoter/enhancer cassette. Both atRA and TTNPB were highly active producing activity in that assay; both compounds interact well with the RARs (Ki values in the 0.2 to 5 nM range). 4-HPR was approximately 1000-fold less potent than atRA and TTNPB in activating the reporter system. 4-HPTTNPB was around 100-fold less potent than atRA and TTNPB in the reporter assay. Because 4-HPTTNPB did not show any significant binding to the RAR proteins, the activity in the reporter gene assay may be due to partial hydrolysis of 4-HPTTNPB to TTNPB, which is active in this system. (See FIG. 13).

Figure 14:
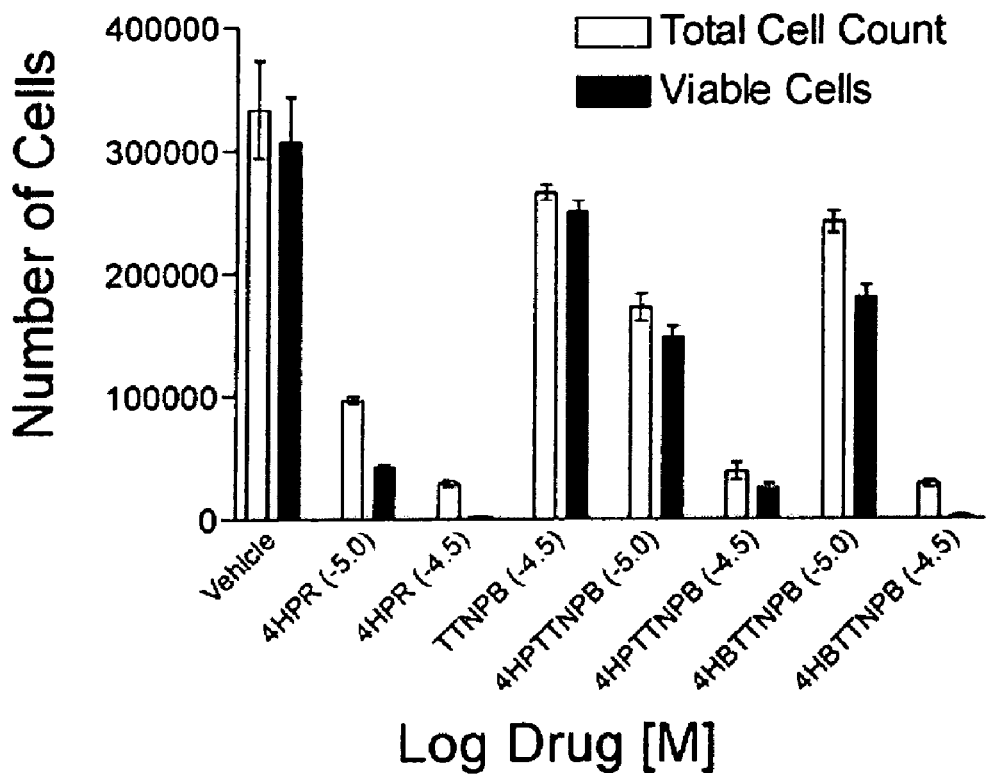
FIG. 14 is a graph of the results obtained from a cell growth inhibition assay, whereby MCF-7 cells were treated once with varying concentrations of retinoids to determine the relative potency of each compound to inhibit cell growth 72 hours later.

Cell growth inhibition assay. MCF-7 cells were treated with varying concentrations of retinoids at the start of the assay and maintained in culture for 72 hours after which the number of live (viable) and total (viable+dead) cells were determined. The response of cells to micromolar doses of 4-HPR was cell death, whereas TTNPB was nearly ineffective in causing the death of cells. Exposure of cells to increasing concentrations of 4-HPTTNPB or 4-HBTTNPB resulted in a dose-dependent decrease in the total number of live cells after 72 hours. (See FIG. 14).

Figure 15:
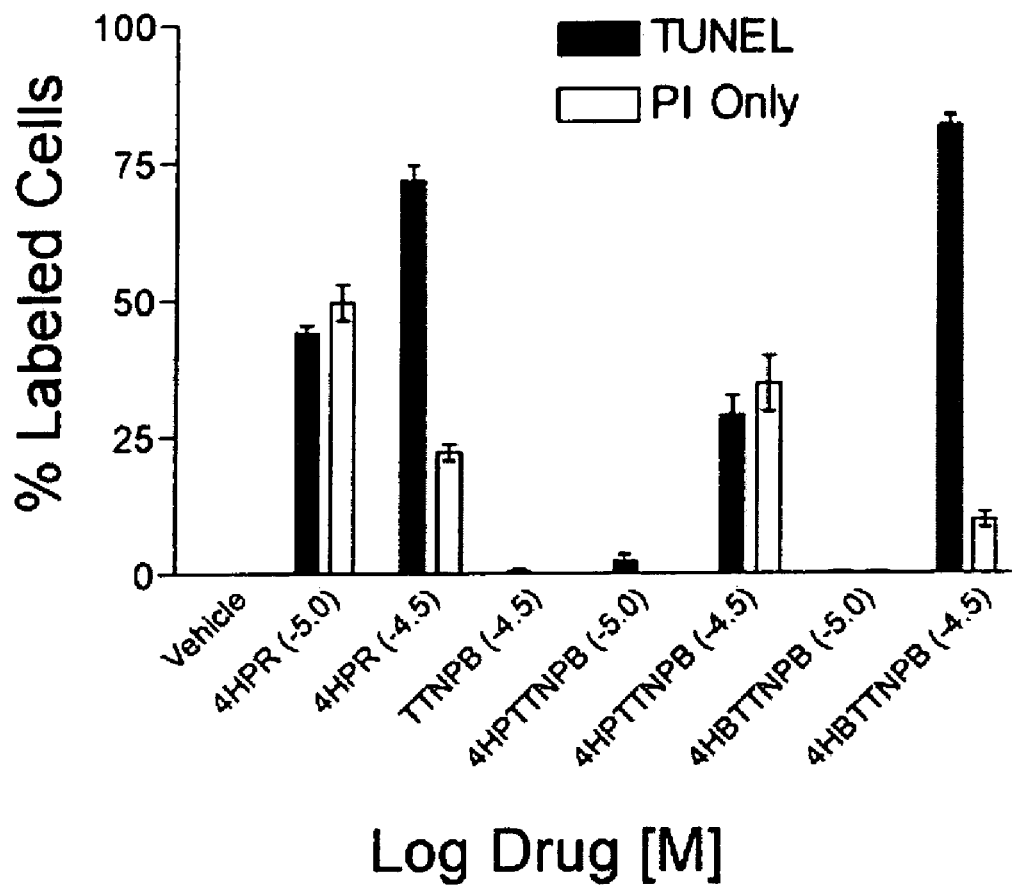
FIG. 15 is a graph showing data obtained using a TUNEL assay to investigate cell apoptosis in MCF-7 cells after exposure to a single dose of various retinoid compounds for 72 hours.

DNA fragmentation. The TUNEL assay (which measures DNA fragmentation) was used to determine whether any of the tested compounds induced cellular apoptosis. Propidium iodide staining (in the absence of TUNEL labeling) was used to measure the number of cells exhibiting necrosis or late-stage aptosis. As previously described, 4-HPR induced a high degree of apoptosis in MCF-7 cells at the concentrations tested. (See Chapman J S et al., Hydrolysis of 4-HPR to atRA occurs in vivo but is not required for retinamide-induced apoptosis, *Arch Biochem Biophys*, 419, pp. 234-243 (2003)). In contrast, TTNPB was ineffective at inducing DNA fragmentation after 72 hours, whereas both 4-HPTTNPB and 4-HBTTNPB at the highest doses were very active at inducing apoptosis after 72 hours. (See FIG. 15). Thus, modification of the TTNPB molecule in that fashion produced a dramatic and unexpectedly superior improvement in biological characteristics and activity.

Teratogenicity testing. The ability of compounds to induce fetal malformations was assessed by giving pregnant rats a single oral dose of compound at the stage of embryogenesis when development is highly perturbed by administration of retinoid compounds. A 0.66 micomoles/kg dose of 4-HPTTNPB was administered as a single oral bolus dose to three pregnant rats at embryonic day 9.25. Such dosing produced profound effects on the outcome of pregnancy in all animals. A very high percentage (>80%) of the fetuses at embryonic day 21.5 were either dead or resorbed. (See Table 1). The few that were alive were all profoundly malformed (e.g., open neural tube, cleft palate and mermaidism). In contrast, the non-hydrolyzable analog, 4-HBTTNPB, administered at the same molar concentration and at the exact same time during pregnancy did not produce any similar adverse effects, and it led to the production of fetuses at E21.5 that were indistinguishable from the vehicle-treated control fetuses. The number of dead and resorbed fetuses also did not differ between the vehicle and 4-HBTTNPB groups. Thus, 4-HBTTNPB at such dose was devoid of any observable teratogenic activity.

Collectively, these data suggest that 4-HPTTNPB shares some characteristics inherent in TTNPB and 4-HPR whereas 4-HBTTNPB is most like the non-hydrolyzable 4-HPR analog, 4-HBR. Without being bound to any theory, TTNPB-like activity in cell culture may result from hydrolysis of 4-HPTTNPB liberating small amounts of TTNPB. In addition, 4-HPTTNPB may induce cell apoptosis reflecting activity of intact 4-HPTTNPB or an unknown metabolite thereof mirroring activity similar to 4-HPR. This is supported by the activity of the non-hydrolyzable analog, 4-HBTTNPB, which induces apoptosis at similar concentrations, but cannot liberate TTNPB. Finally, the potent effect of 4-HPTTNPB on producing teratogenic effects and the complete absense of such effects due to 4-HBTTNPB supports the sypothesis that TTNPB-like activity in vivo results from the hydrolysis of 4-HPTTNPB to liberate small amounts of TTNPB.

Cell culture. The human mammary carcinoma cell line, MCF-7, may be obtained from the American Type Culture Collection (Mannassas, Va.). MCF-7 cells may be maintained in DMEM (Sigma-Aldrich) medium supplemented with 4 g/L glucose, 3.7 g/L sodium bicarbonate and 10% fetal calf serum.

Assay for cell growth inhibition. Cells are plated in flasks/wells of a tissue culture dish. After 24 hours, cells are dosed with a compound of the present invention at varying concentrations, and after 72 hours, the cells are removed from flasks/plates and counted. Fluorescence (due to staining of cells with fluorescein diacetate) was used to count the number of live cells. Phase-contrast microscopy is used to count the total number of cells.

Anti-proliferative activity of compounds 12, 23, 25, 29, 30 and 33 (against MCF-7 human mammary tumor cell culture models) may be determined using the protocol set forth herein. The data would show that each compound inhibits growth of MCF-7 cells in a dose-dependent manner. The data would also demonstrate the utility of each compound to inhibit cancer cell growth.

Competition binding studies may also be performed as set forth herein using compounds 23 (4-HBTTNPB), 12 (propyl analog of 4-HPTTNPB), 25 (O-linked glucuronide of 4-HBTTNPB), 29 ($CH_2$-linked glucuronide of 4-HBTTNPB), 30 ($CH_2$-linked glucose of 4-HBTTNPB) and 33 (O-linked glucose of 4-HBTTNPB) and comparing these results to those obtained for 4-HPTTNPB.

Competition binding to RARs. Compounds 12 and 23 bind only very weakly to RARs, and are thus comparable to 4-HPTTNPB. Compounds 25, 29, 30 and 33 are only slightly better at binding to RARs than 4-HPTTNPB.

Competition binding to RXRs. Compounds 12 and 23 would be comparable to 4-HPTTNPB and show only slight binding competition. Compounds 25, 29, 30 and 33 are no better at binding to RXRs than 4-HPTTNPB.

Reporter gene assay studies may be performed as set forth herein using compounds 23 (4-HBTTNPB), 12 (propyl analog of 4-HPTTNPB), 25 (O-linked glucuronide of 4-HBTTNPB), 29 ($CH_2$-linked glucuronide of 4-HBTTNPB), 30 ($CH_2$-linked glucose of 4-HBTTNPB) and 33 (O-linked glucose 4-HBTTNPB). The results may be compared to data obtained concerning 4-HPTTNPB which is set forth below.

Reporter Gene Assay: Compound 23 may be less active than 4-HPTTNPB (unable to undergo hydrolysis). Compound 12 may also be less active than 4-HPTTNPB, and it may liberate a metabolite that is inactive at RAR binding. Compounds 25, 29, 30 and 33 may be less active than 4-HPTTNPB.

Cell growth inhibition assays may be performed as set forth herein using compounds 23 (4-HBTTNPB), 12 (propyl analog of 4-HPTTNPB), 25 (O-linked glucuronide of 4-HBTTNPB), 29 ($CH_2$-linked glucuronide of 4-HBTTNPB), 30 ($CH_2$-linked glucose of 4-HBTTNPB) and 33 (O-linked glucose of 4-HBTTNPB). The data may be compared to data concerning 4-HPTTNPB which is set forth below.

Cell growth inhibition assay. Compound 23 is similar in activity to 4-HPTTNPB (unable to undergo hydrolysis). Compound 12 may also be less active than 4-HPTTNPB, and it may liberate a metabolite that was RAR inactive at binding. Compounds 25 and 29 are less active than 4-HPTTNPB, and compounds 30 and 33 are similar in activity to 4-HPTTNPB.

DNA fragmentation studies may be performed as set forth herein using compound 23 (4-HBTTNPB). Compound 23 may possess activity similar to 4-HPTTNPB in the DNA fragmentation study. Compounds 25 and 29 are less active than 4-HPTTNPB, and compounds 30 and 33 are similar in activity to 4-HPTTNPB.

Studies investigating the inhibition of DMBA-induced mammary tumors may be performed using compounds 23 (4-HBTTNPB), 25 (O-linked glucuronide of 4-HBTTNPB), 29 ($CH_2$-linked glucuronide of 4-HBTTNPB), 30 ($CH_2$-linked glucose of 4-HBTTNPB), and 33 (O-linked glucose of 4-HBTTNPB. Compounds 23, 25, 29, 30 and 33 may be active and demonstrate little, if any, toxicity.

Studies investigating the teratogenic potential are performed using compounds 23 (4-HBTTNPB), 25 (O-linked glucuronide of 4-HBTTNPB), 29 ($CH_2$-linked glucuronide of 4-HBTTNPB), 30 ($CH_2$-linked glucose of 4-HBTTNPB) and 33 (O-linked glucose of 4-HBTTNPB). Surprisingly and unexpectedly, the data will demonstrate that compounds 23, 25, 29, 30 and 33 possess little, if any, observable embrotoxicity.

The compounds of the present invention are useful in treating cellular proliferative disorders such as breast cancer.

All references cited herein are specifically incorporated by reference in their entireties and for all purposes as if fully set forth herein.

We claim:

1. A compound according to the formula

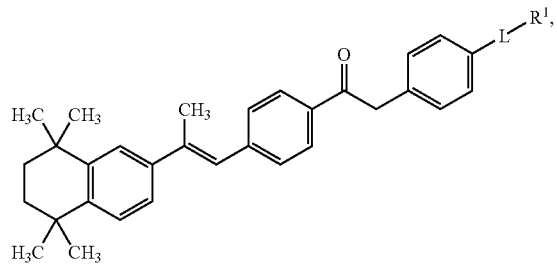

wherein L is a member selected from the group consisting of a single bond, $CH_2$, and O, and,
wherein $R^1$ is a member selected from the group consisting of an aldose moiety,

and, $C_{1-6}$ straight or branched chain alkyl group, and salts, esters and solvates thereof.

2. The compound of claim 1,
wherein L is O, and,
wherein $R^1$ is the aldose moiety.

3. The compound of claim 2,
wherein the aldose moiety is a member selected from the group consisting of:

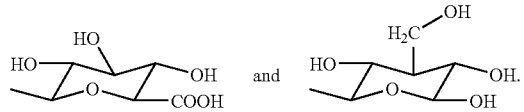

4. The compound of claim 1,
wherein L is $CH_2$, and,
wherein $R^1$ is the aldose moiety.

5. The compound of claim 4, wherein the aldose moiety is a member selected from the group consisting of:

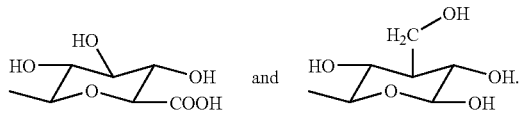

6. The compound of claim 3, wherein the aldose moiety is

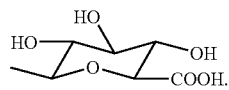

7. compound of claim 3, wherein the aldose moiety is

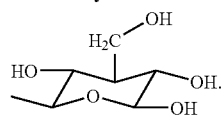

8. The compound of claim 5, wherein the aldose moiety is

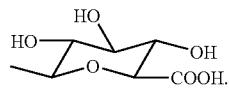

9. The compound of claim 5, wherein the aldose moiety is

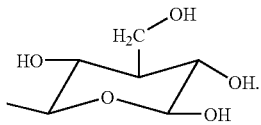

10. The compound of claim 1, wherein L is O, and, wherein $R^1$ is a $C_{1-6}$ straight or branched chain alkyl group.

11. The compound of claim 4, wherein the $C_{1-6}$ straight or branched chain alkyl group is a member selected from the group consisting, of —$CH_3$ and —$CH(CH_3)_2$.

12. The compound of claim 1, wherein L is O, and, wherein $R^1$ is

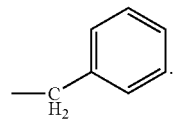

13. The compound of claim 1, wherein L is the single bond.

14. A compound according to the formula

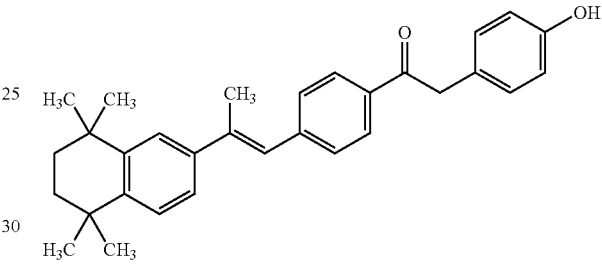

and salts and solvates thereof.

15. A method of treating breast cancer in a human comprising administering to the human a therapeutically effective amount of any one of the compounds of claims 1-14.

* * * * *